(12) United States Patent
Fukunaga et al.

(10) Patent No.: US 7,261,105 B2
(45) Date of Patent: *Aug. 28, 2007

(54) BREATHING CIRCUITS HAVING UNCONVENTIONAL RESPIRATORY CONDUITS AND SYSTEMS AND METHODS FOR OPTIMIZING UTILIZATION OF FRESH GASES

(75) Inventors: Atsuo F. Fukunaga, Palos Verdes Peninsula, CA (US); Blanca M. Fukunaga, Palos Verdes Peninsula, CA (US); Alex S. Fukunaga, Palos Verdes Peninsula, CA (US)

(73) Assignee: F-Concepts LLC, Rancho Palos Verdes, CA (US)

( * ) Notice: Subject to any disclaimer, the term of this patent is extended or adjusted under 35 U.S.C. 154(b) by 538 days.

This patent is subject to a terminal disclaimer.

(21) Appl. No.: 10/777,772

(22) Filed: Feb. 12, 2004

(65) Prior Publication Data

US 2004/0194781 A1  Oct. 7, 2004

Related U.S. Application Data

(63) Continuation-in-part of application No. 10/390,070, filed on Mar. 14, 2003, which is a continuation-in-part of application No. 10/254,700, filed on Sep. 24, 2002, now Pat. No. 6,874,500.

(60) Provisional application No. 60/340,206, filed on Dec. 12, 2001, provisional application No. 60/324,554, filed on Sep. 24, 2001.

(51) Int. Cl.
*A61M 16/00* (2006.01)

(52) U.S. Cl. .................... 128/204.18; 128/203.12; 128/911

(58) Field of Classification Search .......... 128/202.27, 128/203.12, 204.18, 205.11, 207.14, 911, 128/912

See application file for complete search history.

(56) References Cited

U.S. PATENT DOCUMENTS

| | | | |
|---|---|---|---|
| 3,556,097 A | 1/1971 | Wallace | |
| 3,713,440 A | 1/1973 | Nicholes | |
| 3,856,051 A | 12/1974 | Bain | |
| 4,007,737 A | 2/1977 | Paluch | |
| 4,148,732 A | 4/1979 | Burrow et al. | |
| 4,188,946 A | 2/1980 | Watson et al. | |
| 4,232,667 A | 11/1980 | Chalon et al. | |
| 4,265,235 A | 5/1981 | Fukunaga | |
| 4,269,194 A | 5/1981 | Rayburn et al. | |
| 4,318,398 A | 3/1982 | Oetjen et al. | 128/201.13 |
| 4,367,769 A | 1/1983 | Bain | 138/114 |
| 4,391,271 A | 7/1983 | Blanco | |
| 4,453,543 A | 6/1984 | Kohnke et al. | 128/205.12 |
| 4,462,397 A | 7/1984 | Suzuki | |
| 4,463,755 A | 8/1984 | Suzuki | |
| 4,596,246 A | 6/1986 | Lyall | |
| 4,621,634 A | 11/1986 | Nowacki et al. | |
| 4,637,384 A | 1/1987 | Schroeder | |
| 4,657,532 A | 4/1987 | Osterholm | |
| 4,676,239 A | 6/1987 | Humphrey | 128/203.12 |
| 4,809,706 A | 3/1989 | Watson et al. | |
| 4,838,258 A | 6/1989 | Dryden et al. | |
| 4,938,210 A | 7/1990 | Shene | 128/203.12 |
| 4,967,744 A | 11/1990 | Chua | 128/204.18 |
| 5,002,050 A | 3/1991 | McGinnis | 128/203.11 |
| 5,088,486 A | 2/1992 | Jinotti | |
| 5,121,746 A | 6/1992 | Sikora | 128/203.12 |
| 5,140,983 A | 8/1992 | Jinotti | |
| 5,195,527 A | 3/1993 | Hicks | |
| 5,230,727 A | 7/1993 | Pound et al. | |
| 5,284,160 A | 2/1994 | Dryden | |
| 5,320,093 A | 6/1994 | Raemer | |
| 5,377,670 A | 1/1995 | Smith | 128/204.17 |
| 5,398,675 A | 3/1995 | Henkin et al. | 128/203 |
| 5,404,873 A | 4/1995 | Leagre et al. | |
| 5,546,930 A | 8/1996 | Wikefeldt | |
| 5,623,922 A | 4/1997 | Smith | 128/204.18 |
| 5,715,815 A | 2/1998 | Lorenzen et al. | |
| 5,722,391 A | 3/1998 | Rosenkoetter et al. | |
| 5,778,872 A | 7/1998 | Fukunaga et al. | 128/202.27 |

| | | | |
|---|---|---|---|
| 5,823,184 A | 10/1998 | Gross | 128/294.18 |
| 5,901,705 A | 5/1999 | Leagre | |
| 5,983,891 A | 11/1999 | Fukunaga | 128/200.24 |
| 5,983,894 A | 11/1999 | Fukunaga et al. | 128/205.29 |
| 5,983,896 A | 11/1999 | Fukunaga et al. | 128/207.14 |
| 6,003,511 A | 12/1999 | Fukunaga et al. | 128/202.27 |
| 6,079,410 A | 6/2000 | Winefordner et al. | |
| 6,129,082 A | 10/2000 | Leagre | |
| 7,178,521 B2* | 2/2007 | Burrow et al. | 128/202.27 |
| 2005/0150505 A1 | 7/2005 | Burrow et al. | 128/911 |

FOREIGN PATENT DOCUMENTS

| | | |
|---|---|---|
| AT | 93941 | 8/1923 |
| EP | 0 462 412 A2 | 12/1991 |
| EP | 0 982 044 A2 | 8/1999 |
| EP | 0 982 044 A3 | 8/1999 |
| EP | 01 11 7999 | 12/2001 |
| EP | 05 07 7222 | 8/2006 |
| GB | 1 270 946 | 4/1972 |
| WO | WO 85/05277 | 12/1985 |
| WO | WO 91/19527 | 12/1991 |
| WO | WO 98/26710 | 12/1996 |
| WO | WO 01/08736 A1 | 8/2001 |
| WO | PCT/US03/08292 | 12/2003 |

OTHER PUBLICATIONS

Nunn, J.F., *Applied Respiratory Physiology with special reference to anaesthesia*, London, Butterworths, 1971.
Eger, E.I. II, "Anesthetic Systems: Construction and Function", *Anesthetic Uptake and Action*, Baltimore, Williams & Wilkins, 1974 pp. 206-227 (1974).
Eger, E.I. II et al., "The Effect of Inflow, Overflow and Valve Placement on Economy of the Circle System", *Anesthesiology*, pp. 29:93-100 (1968).
Mentell, O. et al., "A new hybrid anaesthetic circuit for a low-flow rebreathing technique", *Acta Anaesthesiologica Scandinavica*, pp. 38:840-844 (1994).
Andrews, J. Jeffrey, *Inhaled Anesthetic Delivery Systems*, Anesthesia, Fourth Edition, pp. 185; and 203-207.
Byrick, R.J., et al., "Rebreathing and Co-Axial Circuits: A Comparison of the Bain and Mera F", *Canad. Anaesth. Soc. J.*, vol. 28, pp. 321-328 (1981).
Dorsch, Jerry A., M.D., Dorsch, Susan E., M.D., *Understanding Anesthesia Equipment*, Chapter 7, The Circle Absorption System, pp. 201-202 and 220-221.
Forrest, P.R., "Defective Anaesthetic Breathing Circuit", *Canad. J. Anaesth.*, vol. 34, pp. 541-542 (1987).
Goresky, G.V., "Bain Circuit Delivery Tube Obstructions", *Canad. J. Anaesth.*, vol. 37, p. 385 (1990).
Hannallah, R., et al., "A Hazard Connected With Re-Use of the Bain's Circuit: A Case Report", *Canad. Anaesth. Soc. J.*, vol. 21, pp. 511-513 (1974).
Heath, P.J., et al., "Modified Occlusion Tests for the Bain Breathing System", *Anaesthesia*, vol. 46, pp. 213-216 (1991).
Jeretin, S. et al., "A Variable Deadspace Device for Use with the Engström Respirator", *Anesthesiology*, vol. 34, pp. 576-577 (1971).
Okazaki, et al., "Effect of Carbon Dioxide (Hypocapnia and Hypercapnia) on Regional Myocardial Tissue Oxygen Tension in the Dog", *Anesthesiology*, vol. 71, No. 3A, A486 (1989).
Okazaki, et al., "Effect of Carbon Dioxide (Hypocapnia and Hypercapnia) on Regional Myocardial Tissue Oxygen Tension in Dogs with Coronary Stenosis", *Anesthesiology*, vol. 73, No. 3A, A549 (1990).
Okazaki, et al., "Effect of Carbon Dioxide (Hypocapnia and Hypercapnia) on Internal Mammary-Coronary Arterial Bypass Graft Blood Flow and Regional Myocardial Oxygen Tension in the Dog", *Anesthesiology*, vol. 81, No. 3A, A717 (1994).
Paterson, J.G., et al., "A Hazard Associated with Improper Connection of the Bain Breathing Circuit", *Canad. Anaesth. Soc. J.*, vol. 22, pp. 373-377 (1975).
Pilbeam, Susan P., *Mechanical Ventilation*, 2nd Ed., Mosby Year Book, St. Louis, Missouri, pp. 285-286 (1992).
Pontoppidan, H., et al., "Acute Respiratory Failure in the Adult", *The New England Journal of Medicine*, vol. 287, pp. 743-752 (1972).
Robinson, S., et al., "Safety Check for the CPRAM Circuit", *Anesthesiology*, vol. 59, pp. 488-489 (1983).
Scott, P.V., et al., "Variable Apparatus Deadspace", *Anaesthesia*, vol. 46, No. 9, pp. 1047-1049 (1991).
Shapiro, B.A., et al., "Clinical Application of Respiratory Care", *Yearbook Medical Publishers, Inc.*, pp. 351-352 ("Principles of Ventilator Maintenance") (1979).
Stoyka, W., "The Reliability and Usefulness of the Suwa Nomogram in Patients in Respiratory Failure", *The Canadian Anaesthetist' Society Journal*, pp. 119-128 (1970).
Suwa, K., et al., "Change in $Pa_{co2}$ with mechanical dead space during artifical ventilation", *Journal of Applied Physiology*, vol. 24, pp. 556-561 (1968).
Advertisement of the CPRAM™ Coaxial Circuits by Dryden Corporation, Indianapolis, Indiana.
Advertisement of the ACE Breathing Circuit™ by Meridian Medical Systems, Inc., Indianapolis, Indiana.
Fletcher, R., Scott, P. V., Jones, R.P., "The variable deadspace is not necessary," Correspondence reported in *Anaesthesia*, vol. 47, No. 7, pp. 623-624 (1992).
Coetzee, J.F. et al., "Fresh gas flow is not the only derminant of volatile agent consumtion . . . ," British Jounral of Anaesthesia, 88 (1) pp. 46-55 (2002).
Baum, J.A. et al., "Low-flow anaesthesia," Anaesthesia, vol. 50 (Supplement), pp. 37-44 (1995).
Johansson, A. et al., "The Ouotient End-tidal/Inspired Concentration of Sevoflurane in a Low-Flow System," Journal of Clinical Anesthesia, 14, pp. 267-270 (2002).

* cited by examiner

*Primary Examiner*—(Jackie) Tan-Uyen Ho
*Assistant Examiner*—Darwin P Erezo
(74) *Attorney, Agent, or Firm*—Daniel B. Schein, Esq.

(57) ABSTRACT

A breathing circuit comprising first and second conduits is disclosed, wherein at least one of the conduits is a non-conventional conduit. A multilumen unilimb breathing circuit is also disclosed having first and second conduits, wherein when the proximal ends of said first and second conduits are each connected to an inlet and outlet fitting, respectively, movement of the distal end of the first conduit causes a corresponding movement of the distal end of the second conduit. In an embodiment, inner and outer flexible conduits are formed of pleated tubing that is axially extendable and compressible to form a unilimb multilumen respiratory circuit. The pleating provides for axial extension and contraction. The multilumen respiratory circuit can provide a variable rebreathing volume. In an embodiment, at least one tube in a multilumen respiratory conduit is radially collapsible and radially expandable to a maximum radius for carrying respiratory gases to and from a patient. Also disclosed are methods and systems of optimizing utilization of fresh gases during artificial or assisted ventilation, including administering anesthesia.

11 Claims, 10 Drawing Sheets

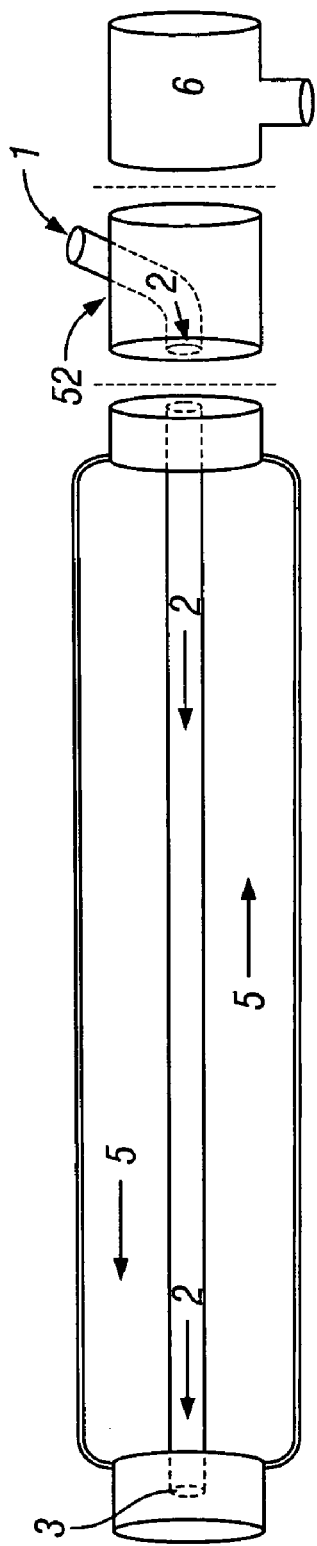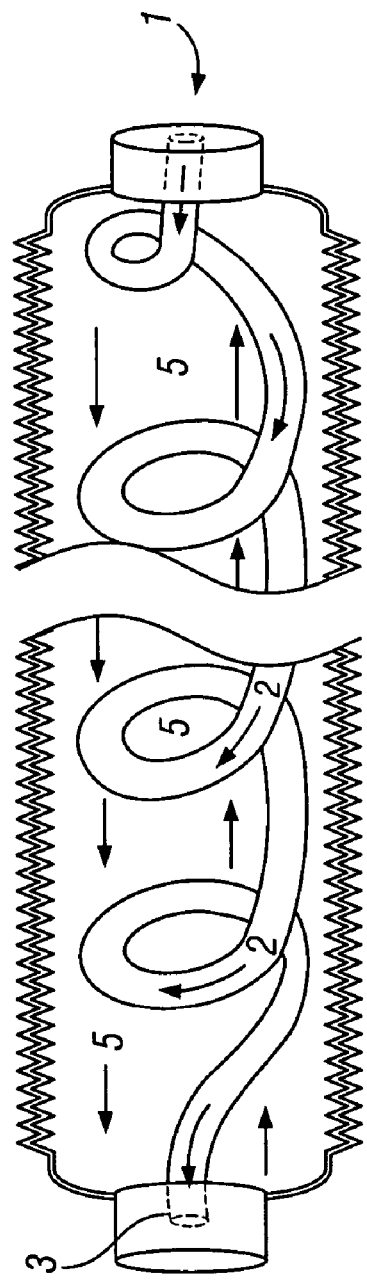
FIG. 4B
FIG. 4C

BREATHING CIRCUITS HAVING UNCONVENTIONAL RESPIRATORY CONDUITS AND SYSTEMS AND METHODS FOR OPTIMIZING UTILIZATION OF FRESH GASES

PRIORITY

This application is a continuation-in-part of U.S. patent application Ser. No. 10/390,070, filed Mar. 14, 2003, which is a continuation-in-part of U.S. patent application Ser. No. 10/254,700, filed Sep. 24, 2002, now U.S. Pat. No. 6,847, 500, which claims priority of U.S. provisional patent application Ser. No. 60/340,206, filed Dec. 12, 2001 and U.S. provisional patent application Ser. No. 60/324,554, filed Sep. 24, 2001, all of which are specifically incorporated by reference as if reproduced in full below.

FIELD OF THE INVENTION

This invention relates to devices for use in resuscitating and/or providing anesthesia and/or assisted and artificial ventilation to patients, and more particularly relates to breathing circuits with interacting mutually adjustable length fluid carrying members, to a multilumen breathing circuit utilizing unconventional (or new era) conduits, and to systems and methods for optimizing utilization of fresh gases (e.g. anesthetic agents and oxygen) during provision of anesthesia and/or assisted and artificial ventilation.

BACKGROUND OF THE INVENTION

Assisted and/or artificial ventilation systems are an essential component of modem medicine. Generally, such systems provide inspiratory fresh gases to a patient from a source of same, such as from an anesthesia or a ventilator machine, and conduct expired gases away from the patient. Inspiratory gases are conducted through a different conduit from the expired gases and thus at least two conduits are required. Commonly used circuits have two limbs (e.g., two independent tubes). The ends of the tubes in a breathing circuit are generally held in spaced relationship by a connector located at the patient, or distal, end of the circuit. The connector can place the distal (i.e., patient) ends of the tubes in a fixed parallel relationship, or the connector can be a Y-piece with the two tubes converging at an angle. Conventional respiratory tubes are corrugated and flexible to permit movement while minimizing collapse and kinking of the tubes. Recently, the use of axially expandable and contractible pleated ("accordion-like") tubing has become popular. Commonly used accordion-like or pleated tubing is known as ULTRA-FLEX® (available from King Systems Corporation, Noblesville, Ind., U.S.A.), FLEXITUBE® or ISOFLEX™, in which the length can be adjusted by axially expanding or contracting one or more pleats between a closed and open position. Whether the pleats are in the open or closed position, the tube wall remains corrugated to minimize the risk of kinking or collapse upon convolution or bending of the tubing.

To facilitate examination, the background sections of the U.S. non-provisional and provisional patent applications from which priority is claimed should be referred to. For further information on breathing systems, and anesthetic and assisted ventilation techniques, see U.S. Pat. Nos. 3,556, 097, 3,856,051, 4,007,737, 4,188,946, 4,265,235, 4,463,755, 4,232,667, 5,121,746, 5,284,160, 5,377,670, 5,778,872, 5,901,705, and 5,983,896, Austrian Patent No. 93,941, British Patent 1,270,946, Dorsch, J. A., and Dorsch, S. E., *Understanding Anesthesia Equipment: Construction, Care And Complications* Williams & Wilkins Co., Baltimore (1974), Nunn J. F.: *Applied Respiratory Physiology With Special Reference to Anaesthesia*. London, Butterworths, 1971, Eger E I II (ed): *Anesthetic Uptake and Action*. Baltimore, Williams & Wilkins, 1974 and Andrews, J. J., "Inhaled Anesthetic Delivery Systems," in *Anesthesia*, $4^{th}$ Ed. Miller, Ronald, M. D., Editor, Churchill Livingstone, Inc., N.Y. (1986). The text of all documents referenced herein, including documents referenced within referenced documents, is hereby incorporated by reference as if same were reproduced in full below.

Cost Effective Anesthesia Systems and Unconventional New Era Respiratory Conduits Hospitals, medical personnel, and related entities are always looking for ways to improve medical care. Numerous monitoring standards have been implemented to ensure that the required medical care is being safely administered. For example, in the field of respiratory care and anesthesia, non-invasive and invasive monitoring methods have become routinely used, such as alarm monitoring systems that warn the user of obstruction and/or disconnection of gas flows, inspired and end-tidal gas monitoring, oxygen saturation monitoring by pulse oximeter, arterial blood gas and mixed venous blood gas monitoring. These techniques and devices enable continuous patient monitoring, which permits the vigilant healthcare practitioner to more accurately adjust or titrate the necessary dosages of anesthetic gases or drugs, and readily detect problems due to the pathophysiologic condition of the patient or due to those caused by medical equipment failure or settings. There is a desire for an anesthesia system that can optimize the use of such expensive monitoring equipment, which for example, could be used to decrease the waste of anesthetic gases.

Respiratory care is commonly and increasingly provided in medicine. Respiratory care includes, for example, artificial ventilation techniques, such as assisted ventilation and/ or oxygen therapy. Certain devices widely used in respiratory care include breathing circuits, filters, HME's (heat and moisture exchangers), endotracheal tubes, laryngeal masks, laryngeal tubes, and breathing masks. Breathing circuits comprised of rigid pipes or flexible corrugated tubes made of rubber, plastic or silicon flexible tubes have been widely used all over the world for almost a century. In order to prevent cross contamination, "single use" breathing circuits are disposed of after a single use, or alternatively, more sturdy and more expensive reusable breathing circuit are used that can be sterilized by autoclave or other means. Both types of circuits are expensive to produce and/or use. Sterilization of the circuit requires substantial labor and processing costs, likewise disposing of the breathing circuit after a single use, while it is very effective in preventing cross contamination, also results in additional cost to the hospital.

While prior art devices fulfill their respective, particular objectives and requirements, the aforementioned patents and the prior art do not describe a device wherein at least one of the respiratory conduits is comprised of a non-conventional (also referred to as "new era") pipe or tube (i.e., different from a rigid-walled tube, pipe, corrugated tube, or pleated tube), which is both axially and radially flexible, but which has little or no compliance beyond a certain conduit radius and/or volume. By radially flexible, it is meant that the diameter of the conduit can be substantially reduced or the conduit can be relaxed or collapsed in cross-section in comparison to rigid-walled conventional tubing. This is distinguished from axially bending the tubing without substantially altering the cross-sectional area of the tube at the bend as is possible with rigid-walled prior art tubing. Prior art rigid-walled respiratory conduits maintain patency under ambient conditions as well as under the pressure differentials between their interior and exterior that occur during use for providing inspiratory and/or receiving expiratory gases. Since these prior art respiratory conduits do not radially collapse under ambient conditions (e.g., when not in use), they require greater space for shipping and storage, and they require thicker walls to have sufficient rigidity to avoid collapse under ambient and operating conditions. Thus, a greater amount of plastic is used to produce such tubing, which increases costs, as well as the volume of the waste produced.

In general, circuit compliance (i.e., expansion of the volume of circuit tubing under operating pressures) is undesired as it interferes with the accuracy and precision of gas administration. Further, excessive compliance may lead to insufficient gases reaching the patient's lungs.

The present inventors discovered that, so long as the respiratory conduits, and preferably the inspiratory conduit, can maintain patency for inspiratory and expiratory gases, the conduits do not need to be always patent like rigid-walled pipes or tubes (e.g., corrugated plastic tubes that maintain a fixed diameter at ambient conditions and/or which are relatively rigid or straight). The respiratory conduits of the present invention should, however, provide low resistance and little compliance during use sufficient to meet the requirements for spontaneous and assisted ventilation. It is preferred that the inspiratory conduit permit gas flow at all times, and even under negative pressure, and that the expiratory line provide positive pressure even in spontaneous ventilation.

Pleated tubing (i.e., flexitube) has been used for independent inspiratory and/or expiratory tubing in dual limb circuits, and taught by Fukunaga et al for use in at least the outer tube of a multilumen unilimb circuit. However, it has been discovered by the present inventors that when flexitube is used as the inner conduit within a multilumen unilimb circuit, certain problems not previously recognized were encountered. For example, while the inner and outer tubes can be extended easily by pulling the outer tube distal fitting to which the distal ends of both tubes are attached, contraction may be less smooth than extension due to pinching or interaction of the inner tube pleats with the outer tube pleats. Further, the contour of the passageway formed between the inner and outer tubes in a breathing circuit formed of pleated tubing can cause turbulence and a higher resistance to flow than when smooth walled tubing or standard corrugated tubing is used as the inner tube, whether or not the tubes are coaxial or offset. Flow resistance can change considerably when the tubing of such a circuit is bent, contracted or extended. It was surprisingly discovered that despite the potential problems mentioned above, a unilimb circuit wherein both the first and second tubes, or in a preferred embodiment inner and outer tubes, are pleated tubes can be made without significant obstruction or resistance concerns and in a clinically acceptable size with desirable performance characteristics.

The present inventors have also discovered that, in a unlimb multilumen circuit constructed with an inner tube and outer tube made of pleated tubing, wherein a portion of the outer tube and the inner tube are pleated for axial extension and contraction, the length of the inner tube pleated section can be longer than the length of the outer tube pleated section. This reduces the risk of disconnection of the inner tube, a problem which has caused great concern in the prior art with unilimb circuits having the inner tube connected at its distal end to a distal terminal and at its proximal end to a proximal terminal or proximal fitting.

Multilumen unilimb circuits in the past have been referred to as coaxial even when in fact the center axis of the inner and outer tubes are not coincident, but are either parallel or fluctuate along the length of the circuit, or in instances where the two tubes are merely adjacent to each other. Hence, multilumen circuits include but are not limited to coaxial circuits, and circuits that are referred to as coaxial can be multilumen unilimb circuits wherein one tube is within the other or adjacent to the other to form a unilimb circuit but they do not share a common axis along their length.

Definitions

To facilitate further description of the prior art and the present invention, some terms are defined immediately below, as well as elsewhere in the specification. As used herein, the term "artificial or assisted ventilation" shall also incorporate "controlled and spontaneous ventilation" (i.e., in contrast to controlled or assisted ventilation in spontaneous ventilation the patient breathes on their own) in both acute and chronic environments, including during anesthesia. Fresh gases include gases such as oxygen and anesthetic agents such as nitrous oxide, halothane, enflurane, isoflurane, desflurane, sevoflurane, that are generally provided by a flowmeter and vaporizer. The end of a conduit directed toward a patient shall be referred to as the distal end, and the end of a conduit facing or connected to a source of inspiratory gases shall be referred to as the proximal end. Likewise, fittings and terminals or other devices at the distal end of the breathing circuit, e.g., connecting to or directed at the patient airway device (i.e., endotracheal tube, laryngeal mask, laryngeal tube, face mask etc.), will be referred to as distal fittings and terminals, and fittings and terminals or other devices at the proximal end of the breathing circuit will be referred to as proximal fittings and terminals. So, a distal adaptor or connector would be located at the distal or patient end of a circuit.

It is generally understood that a proximal terminal in a multilumen unilimb breathing circuit context is located at the machine end of the circuit and separates at least two independent flow paths that are in parallel closely-spaced or apposed relationship or that are coaxial in the circuit so that at least one flow path can be connected to a source of inspiratory gases while another flow path can be connected to an exhaust port that is spaced from the inspiratory gas port. A proximal terminal may also comprise a rigid housing that merges two independent flow paths into a common flow path, for example a Y-type fitting, preferably with a septum. The use of a proximal fitting with a proximal terminal in a unilimb circuit is a new concept brought about by the Universal F2® inventions, which for the first time made it possible to readily connect and disconnect plural tubes to a proximal terminal on an assisted ventilation machine via a corresponding proximal fitting. Unlike the proximal terminal, when a proximal fitting comprises multiple lumens, the proximal fitting maintains the spatial relationship of the proximal ends of the tubes forming a multilumen circuit. Hence a proximal fitting in a breathing circuit is to generally be understood as a fitting which permits ready connection of tubing to a proximal terminal which can provide inspiratory gases and exhaust expiratory gases from separate spaced ports. In some embodiments of the present invention tubing may be directly bonded to a proximal terminal, while in other embodiments tubing may connect to a proximal fitting that can engage a corresponding port or ports on a proximal terminal. The proximal fitting may include filter means, or may engage a filter which in turn connects to a proximal terminal.

The term conduit broadly comprises fluid carrying members without being limited to conventionally used corrugated tubes, such as those used in presently available breathing and/or anesthesia circuits (i.e., a conduit has a lumen defined by one or more walls, has a variety of shapes and diameters, and serves the purpose of carrying inspiratory gases to or expiratory gases from a patient). For example, conduits for use with the present inventions may comprise flexible fabric or plastic sheaths (like a film or sheet made of plastic, such as polyvinyl, that can have a cylindrical or tubular form when gases or fluid are contained, but collapses or looses the tubular form when deflated or emptied) and/or flexible tubes that may be smooth-walled, straight, corrugated, collapsible, and/or coiled. In this respect, certain embodiments of the present invention substantially depart from the conventional concept and design of prior art respiratory conduits. Embodiments of flexible conduits for carrying respiratory gases to and/or from a patient in accordance with the present invention can be both flexible in the radial and axial directions up to a maximum volume and/or radius (or maximum cross-sectional area where the cross-sectional shape is not circular), and have a wide variety of cross-sectional shapes, and in so doing provide a low cost apparatus very well suited to providing respiratory care, i.e., assisted ventilation to a patient, which is effective and practical.

Unconventional or non-conventional tubular conduits refer to conduits used in a respiratory circuit for carrying patient inspiratory and/or expiratory gases that are made of materials and/or have shapes not previously used in assisted ventilation or anesthesia machines for carrying inspiratory and expiratory gases between a patient or other mammal and the machine. By carrying patient inspiratory and/or expiratory gases, it is understood that the gases are being provided via a conduit to a patient from a source (e.g., ventilator machine) and exhausted via the same and/or another conduit to an exhaust (e.g., assisted ventilatoin machine). For a example, a coiled inspiratory or expiratory conduit when used in accordance with the present invention is a non-conventional tubular conduit. Likewise, a conduit formed of flexible, gas impermeable fabric, such as but not limited to extruded polyethylene, polypropylene or polyvinyl film, that is radially expandable to a maximum radius and volume under pressures generally used in assisted respiration and is collapsible when the pressure inside of same is less than ambient pressure or the pressures generally used in assisted respiration, can be used as a non-conventional respiratory conduit in accordance with the present invention. Ambient pressure refers to the pressure normally encountered outside of tubes, which is generally atmospheric pressure. Such conduits can maintain patency as needed in use yet readily relax or collapse (collapsing may require some assistance depending on the embodiment) to smaller diameters, lengths, and volumes, particularly when the internal pressure inside is sufficiently lower than the pressure outside of the conduit.

For the purposes of brevity, the term Suave™ flexible tube is used to describe a flexible respiratory conduit for use in carrying respiratory gases (i.e., gases to be inspired and expired gases to be exhausted) between a patient and a ventilation machine or respiratory care device in which the conduit is radially collapsible when not in use, and can expand to a maximum predetermined diameter (or maximum cross-sectional area; maximum diameter and maximum radius incorporate maximum cross-sectional area when the cross-sectional shape is not circular) and volume during use (such a conduit shall be hereinafter referred to in this document as a suave tube or suave conduit; no trademark rights are waived by use of the term suave or any other mark used herein regardless of case or inclusion of the TM or ® symbol). Upon expansion to its maximum diameter (i.e., maximum cross-sectional area) a suave tube exhibits substantially the same compliance in assisted ventilation applications as conventional corrugated tubes or pleated tubing (i.e., ULTRA-FLEX®) conduits. Suave flexible tubes may also be axially expanded or contracted. Suave tubes are much less expensive to manufacture than conventional conduits having a relatively rigid diameter or cross-sectional shape, such as those formed of corrugated tubing.

Preferred radially collapsible tubes for use in the present invention will, when inflated at pressures encountered in providing assisted ventilation and/or anesthesia to humans and other mammals, have a compliance of less than about 50%, preferably less than about 20%, more preferably less than about 10%, even more preferably less than about 5%, and most preferably less than about 2%. Preferred radially collapsible tubes for use in the present invention have a minimum cross-sectional area when fully inflated sufficient to meet the desired flow characteristics (hereinafter, referred to as the inflated cross-sectional area), and can collapse so that the collapsed cross-sectional area is preferably less than about 90% of the inflated cross-sectional area, more preferably less than about 70% of the inflated cross-sectional area, even more preferably less than about 50% of the inflated cross-sectional area, even more preferably less than about 25% of the inflated cross-sectional area, and most preferably less than 10% of the inflated cross-sectional area.

In one embodiment, the suave tubes are shipped and stored in collapsed form, and after inflation thereof no subsequent effort may be made to collapse them, except optionally to compress the suave tubes to a smaller volume for disposal. In this way, manufacture, shipping and storage costs are minimized. Gravitational forces will cause the suave tubes to collapse to varying degrees in some embodiments when not pressurized sufficiently.

Breathing Circuit Requirements

A patient requiring artificial ventilation or anesthesia may be positioned in an awkward position and depending on the surgical site the required length of the circuit may vary. This is also so in patients undergoing diagnosis, e.g., MRI, CT scans, etc. It is therefore desirable to have a breathing circuit that is flexible and that the length of both the inspiratory or fresh gas delivery tube and the expiratory or exhaust tube can be adjusted while minimizing disconnections, obstructions, entangling and kinking. It is also desirable to have breathing circuits that are light in weight. Furthermore, for cost containment, the health care providers (i.e., hospital, physician, ambulatory surgery center, nursing homes, etc.) require inexpensive breathing circuits and/or inexpensive methods to provide artificial ventilation or anesthesia to patients in need thereof.

Breathing circuits may be classified based on how carbon dioxide is eliminated. Carbon dioxide can be eliminated by "washout", which is dependent on the fresh gas inflow (i.e., $CO_2$ absorption is not required, e.g., in a Mapleson type circuit), or by using a $CO_2$ absorber such as soda lime and the like, (i.e., as in a circle circuit). Thus, breathing circuits in anesthesia are generally provided as circle circuits ($CO_2$ absorption system) or Mapleson type circuits. Because Mapleson D type partial rebreathing systems require high fresh gas flows, the circle system is the most widely accepted system. Breathing systems wherein low fresh gas flow can be utilized are advantageous because of reduced consumption and waste of fresh gases (e.g., anesthetic gases), ecological benefits (reduced environmental pollution), and cost-savings. However, a major concern of low flow techniques in anesthesia is the efficiency of fresh gas utilization and the unpredictability concerning the alveolar or inspired concentration of anesthetics provided to the patient that should be administered in sufficient dosages to achieve desired anesthetic endpoints (e.g., avoid awareness during surgery without overdosing). Moreover, there is a significant discrepancy between the volatile anesthetic vaporizer setting concentration and the inspired concentration of anesthetic gases. A further concern with the circle system is the interaction of volatile anesthetics with the carbon dioxide absorber (e.g., soda lime), which has been recently reported as producing toxic substances. This concern includes the formation of carbon monoxide and Compound A during degradation of volatile anesthetics by soda lime. For example, CO has been found in anesthetics, including halothane, enflurane, isoflurane and desflurane circle systems. Moreover, in the case of sevoflurane, it is known that sevoflurane is degraded in the presence of soda lime to olefin and Compound A, which has been reported to have nephrotoxic potential at clinical concentrations. Further, it is desired to reduce waste of expensive anesthetic and respiratory gases in circle systems and Mapleson type systems.

A major concern with prior uililimb breathing circuits is that the inspiratory gas or fresh gas line not become disconnected or blocked (e.g., via kinking) during use. For this reason, rigidly bonding the proximal end of the inspiratory gas line to the fresh gas inlet fitting was stressed, while the distal end was permitted to move with respect to the distal end of the outer conduit (e.g., exhaust conduit), which could create a variable dead space. Despite the surprising discovery reported in U.S. Pat. No. 5,778,872, to Fukunaga, that an appropriate dead space in a breathing circuit could be beneficial by yielding nornocapnia without hypoxia, there is still a desire for a circuit that has either a minimum and/or fixed dead space regardless of circuit manipulation, yet is flexible and safe. Further, there is a desire for systems that more efficiently utilize anesthetic gases in a safe and predictable manner. It is also desired that the same breathing circuit be utilized in both adult and pediatric cases, or at least in a greater number of patients, thereby minimizing the need for circuits of different size. There is also a need for breathing circuits and systems that are simpler, lightweight, cost-effective, safer, and/or easier to operate and handle than prior circuits and systems.

SUMMARY OF THE INVENTION

An embodiment of the present invention includes a breathing circuit, wherein at least one of the respiratory conduits is a non-conventional conduit. Thus, in a unilimb, dual limb or a multilimb circuit, a non-conventional conduit may be used to carry inspiratory and/or expiratory gases between a patient or other mammal and a machine. For example, in an embodiment, at least one tube in the circuit may be a collapsible or suave tube, or may be a spiral or coiled tube. Such circuits may be referred to as F3™ circuits or Universal F3™ circuits (no waiver of trademark rights is made hereby for these or other marks used herein).

An embodiment of the present invention includes a multilumen respiratory circuit comprising first and second conduits, wherein the proximal ends of the first and second conduits can each be connected to a respective inlet or outlet fitting, and movement of the distal end of the first conduit causes a corresponding movement of the distal end of the second conduit. Thus, the circuit members interact so that axial extension or contraction of one member causes a corresponding axial extension or contraction in length of a second member. This latter type of circuit may also be referred to herein as an F3™ contractible circuit or a Universal F3™ circuit. In an embodiment, at least one of the conduits is a coiled tube. In another embodiment, a coiled tube is contained within an outer flexible tube that is axially extendable and compressible, forming a unilimb multilumen respiratory circuit, which may also be referred to herein as an F Coil™ circuit.

In an embodiment, the outer flexible conduit may be a pleated tube or a non-conventional conduit to provide for axial extension and contraction. In an embodiment, an accordion-like tube (e.g., UTLRA-FLEX® tube), is divided internally by a common wall that is made of a flexible plastic or gas-impermeable fabric that allows simultaneous radial expansion of one lumen while causing contraction of the other lumen(s) sharing the common flexible wall. In another embodiment, a non-conventional conduit can be joined side by side with a pleated tube either by continuous or spaced attachment. Further, two or more Suave™ tubes can be used together to create a multi-lumen Suave™ tube respiratory conduit. Such a multi-lumen Suave™ tube respiratory conduit can be manufactured by extruding a tube of flexible plastic in much the same way plastic storage bags are formed. However, rather than heat sealing radially across the extruded tube to form a bag, axial seams can be heat formed in the axial direction to form separate gas carrying lumens.

Proximal and distal fittings can be bonded at the proximal and/or distal ends of the lumens in the respiratory conduit devices of the present invention to facilitate operative connection to machines and patients, respectively.

An embodiment of the present invention includes a multilumen respiratory conduit comprising at least first and second flexible tubes, wherein the proximal ends of the first and second flexible tubes can each be connected to an inlet or outlet fitting, and wherein at least one of the flexible tubes is comprised of a non-conventional plastic tubular material (e.g., formed of a flexible fabric, such as polyvinyl). Such a respiratory conduit is capable of maintaining respiratory patency under the range of conditions encountered in providing respiration, whether spontaneous or assisted ventilation (i.e., affording free passage of inspiratory and expiratory gases), but may partially or substantially completely collapse when not in use. Such a tube can be shipped in collapsed or substantially collapsed form. The tubes forming the multilumen respiratory conduit can be arranged side by side, have periodic connections to one another, or one can be contained within another, and their shapes can be greatly varied. For example, a circular cross-sectional shape is not necessary. The distal and proximal ends of each tube can be formed of a more rigid material than the rest of the tube or be bonded to a fitting to facilitate connection to an inspiratory gas source, an exhaust outlet, to a carbon dioxide canister for recirculation of gases such as that used in an anesthesia machine, and to airway devices such as respiratory masks and endotracheal tubes.

Another embodiment of the present invention includes a unilimb multilumen respiratory circuit comprising first and second conduits, wherein the proximal ends of the first and second conduits can each be connected to a respective inlet or outlet contained in a common proximal fitting, and the distal ends can be connected to a common distal fitting or connector, and movement of the distal end of the first conduit causes a corresponding movement of the distal end of the second conduit. Thus, the circuit members interact so that axial extension or contraction of one member causes a corresponding axial extension or contraction in length of a second member.

Consideration should be given to whether the conduits have laminar flow or turbulent flow. Since generators of turbulence such as sharp bends and sudden changes in diameters are the most important sources of resistance, a screening test for resistance should be made to generate an optimal combination of the conduits particularly when a tube within a tube configuration is used. Preferably, the resistance should be less than about 1 cmH2O pressure drop at 10 L/min or about 6 cmH2O pressure drop at 60 L/min respectively. Therefore, the resistance screening test of the first and second conduits should be done when the circuit is extended, compressed, semi-extended and with a number of bends at various flow rates (e.g., 10 L/min to about 60 L/min). The resistance should be within the acceptable ranges as mentioned above (i.e., low resistance) to meet the requirements for spontaneous or assisted ventilation for the circuit to function safely.

In an embodiment, the distal fitting or connector provides means to prevent obstruction of inspiratory and expiratory functions. In a preferred embodiment, the circuit is formed of first and second conduits wherein the conduits are formed of flexible, axially extendable and compressible pleated tubing (i.e., flexitube or accordion-like tube). Such tubing maintains a minimum radius, yet will also substantially maintain a length and/or angular shape to which it is manipulated. The accordion-like pleats permit the tube to expand and contract to a predetermined degree associated with the amplitude of the pleats and the maximum and minimum angle formed by the annular wall portions meeting to form the pleats. It is desired in an embodiment that expansion and contraction of the first and second tubes be done in a synchronized manner, particularly when a smaller diameter first tube is contained within a larger diameter second tube. Further, the expanded length of the inner tube is preferably slightly longer than the outer tube expanded length (e.g., about 3 to 5 pleats) so as to minimize disconnection risks at the distal or proximal end connectors or fittings when manipulation, expansion and contraction of the circuit is done.

Hence, an additional embodiment of the present invention involves the use of a pleated inner tube in any unilimb circuit having an inner tube within an outer tube, wherein the outer tube is of fixed length, and the distal ends of the inner and outer tubes are connected to a common distal fitting and the proximal ends of the inner and outer tubes are connected to a common proximal fitting or terminal. In a preferred embodiment, if the pleated inner tube is not constrained between the distal and proximal fittings by common connection thereto with the outer tube (i.e., before connection of the outer tube to both fittings over the inner tube), the inner tube can be axially compressed to a length equal to or less than the fixed length of the outer tube or axially extended to a length greater than the fixed length of the outer tube. This reduces the risk of detachment of the inner tube from the fittings.

The present invention also involves new systems and methods of optimizing utilization of fresh gases during artificial or assisted ventilation, including administering anesthesia. In an embodiment, a Mapleson D type system is modified and combined with a modified $CO_2$ absorption circle system to produce an efficient system, wherein the system is capable of optimizing the utilization of anesthetic gases in a safe and predictable manner. By providing undiluted fresh gases at the patient side (i.e., distal end of the circuit) and circulating the expired gases through a scrubber circuit having a carbon dioxide absorber, the system provides assurance that the patient receives more accurate fresh gas concentrations (i.e., close to the anesthesia machine flow meter's oxygen concentration and the volatile anesthetic vaporizer's concentration setting). In addition, recirculating the gases allows re-use of the gases after $CO_2$ elimination, thereby providing reliable low flow anesthesia. As a result, utilization of fresh gases is optimized. Furthermore, by using a unilimb multilumen breathing circuit wherein the dimensions of at least one of the breathing conduits can be altered to adjust the volume therein or by using mutually adjustable length members (e.g., with flexitube members), the anesthetic concentration and amount of rebreathing can be safely adjusted and predictably optimized, and the same breathing conduit or circuit may be utilized universally in adult and pediatric cases.

The present invention may be better understood by reference to the figures and further detailed description below. For the purposes of facilitating understanding of the invention, in the following figures certain fitting components are not shown and/or certain fitting components are shown in simplified form. For example, struts or flanges for spacing components from one another are not shown, wall thickness and relative tube diameters and lengths are not to scale, and/or the proximal terminal to which the proximal fitting can be connected is not shown.

DESCRIPTION OF THE FIGURES

FIG. 4A-C illustrate the components and operation of a system constructed in accordance with the present invention, with 4B&C illustrating the system using a coil within a tube circuit embodiment of the present invention, in which the outer tube is an accordion-like tube (e.g., Ultra-Flex®).

DETAILED DESCRIPTION OF THE INVENTION

F3™ Circuits—Circuits with Unconventional (New Era) Conduits

Figure 1:
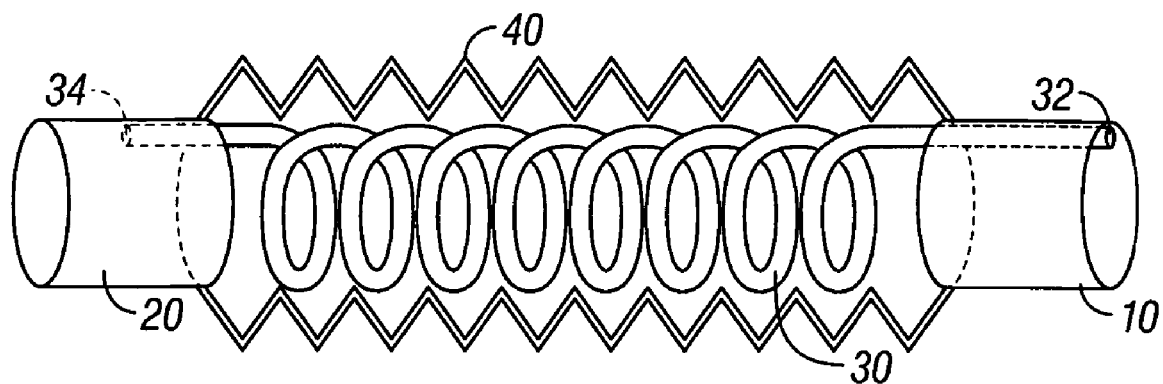
FIG. 1 is a diagram illustrating a retracted first, coiled-tube conduit contained within a compressed second conduit, with both the proximal ends of the first and second conduits being attached to a common proximal fitting, wherein a portion of the second conduit is not shown to permit viewing of the first conduit.

With reference to FIG. 1, an embodiment of the present invention is illustrated, including a multilumen breathing circuit with interacting mutually adjustable length members. This embodiment, also referred to herein as the F-Coil™ circuit, has optional proximal fitting 10 and an optional distal fitting 20. First conduit 30 is a coiled resilient tube having a proximal end 32 and a distal end 34. Proximal end 32 of first conduit 30 is connected to proximal fitting 10 and distal end 34 of first conduit 30 is connected to distal fitting 20. In an alternative embodiment, proximal fitting 10 may provide a proximal connector for tube 30. End 32 and fitting 10 may vary in diameter, shape and spatial relationship to provide for connection to any standard "F2™ type" proximal terminal, such as that described in U.S. Pat. No. 5,778,872, to Fukunaga.

In a preferred embodiment, the second or outer tube 40 is flexible and corrugated, and formed of a transparent (or semi-transparent) material. Preferred corrugated tubing includes, for example ULTRA-FLEX®, which upon axial extension from its compressed axial conformation, or vice versa, will retain its axial length (e.g., will not rebound; i.e., accordion-like pleated tubing). Further, the ULTRA-FLEX®, when bent, will retain the angle of curvature to which it is bent without substantial reduction in the tube's inner diameter. Suitable corrugated tubing for use in the present invention is used in the Ultra-Flex circuit, ULTRA-FLEX® tubing from King Systems Corporation, of Noblesville, Ind., U.S.A., or the tubing used in the Isoflex™ circuit sold by Baxter Corporation of Round Lake, Ill., USA. The tubing may be formed with integral distal and/or proximal fittings, wherein the fittings have relatively thicker or more rigid walls than the tubing, or the tubing can be bonded or welded to appropriately shaped fittings as desired.

As should be abundantly clear to one of skill in the art from the forgoing summary and definitions, there are many embodiments of the present invention that are envisioned and encompassed. For example, diameters of first and second conduits (30, 40) may vary depending on use. Also, outer tube 40 or inner tube 30 may be replaced with a suave tube. It should be clear that a coiled flexible tube may change its overall axial configuration without altering the cross-sectional shape of the lumen or lumens within it.

The outer tube 40 ends in an optional distal outer fitting 20, which is designed for ready connection to patient devices, such as an endotracheal tube, laryngeal tube, laryngeal mask or anesthesia mask.

In an embodiment, the distal end 34 of the first tube may be directly bonded to the interior of second tube 40. Optionally, the first tube may be directly bonded to the interior of second tube 40 at a series of designated points along the length of tube 40. First tube 30 may also be wrapped around the exterior of tube 40, and periodically bonded to the exterior thereof.

With reference to optional distal fitting 20, the distal end 34 of first tube 30 is shown bonded thereto. In an embodiment, distal fitting 20 is connected to an optional inner distal fitting to which the distal end 34 of first tube 30 may be connected. The length of fitting 20 may be extended and the connection point between fitting 20 and the optional distal inner fitting made axially adjustable, wherein a predetermined dead space may be provided.

Figure 2:
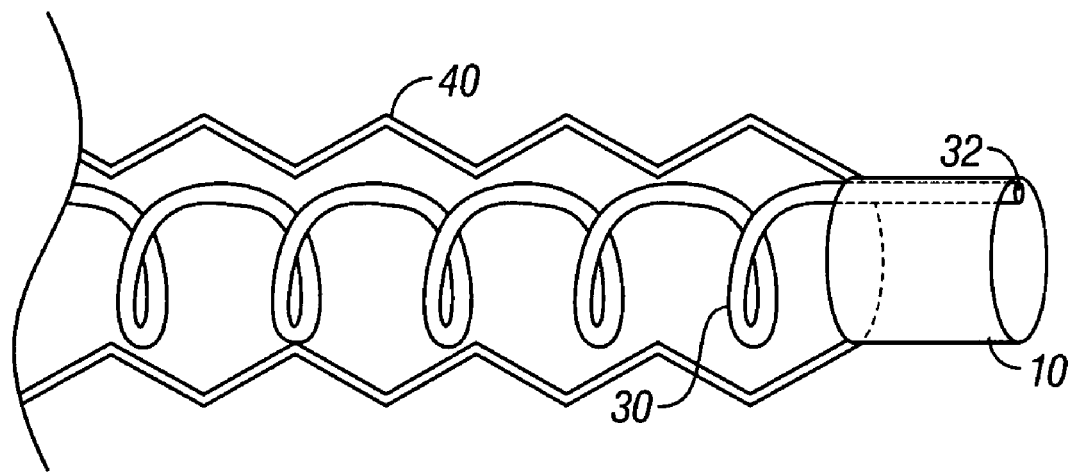
FIG. 2 is a diagram illustrating a portion of the device of FIG. 1 upon extension.
Figure 3:
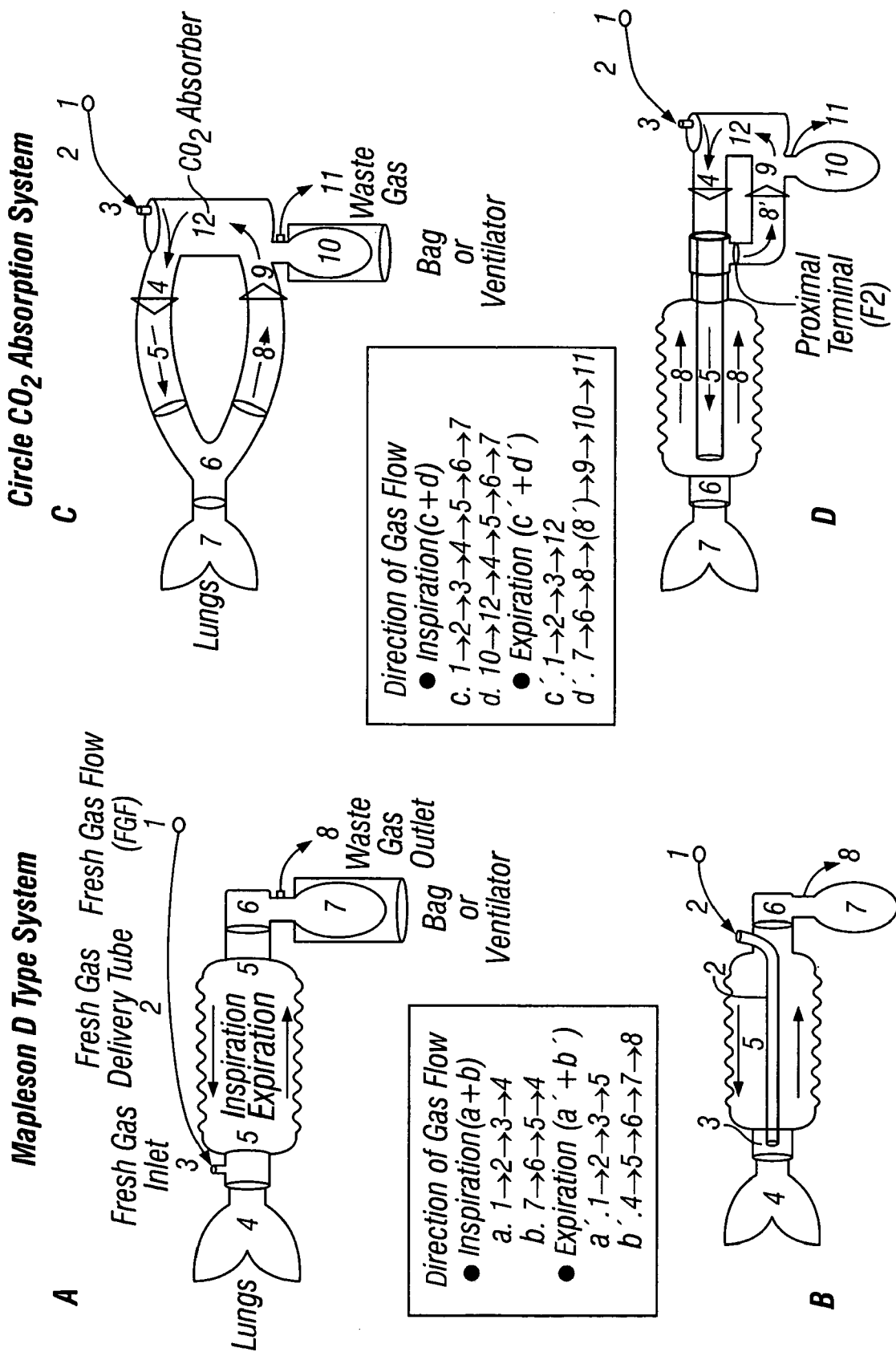
FIG. 3A-D illustrate the operation of a Mapleson D type system and Circle $CO_2$ Absorption System.

With reference to FIG. 2, it can be seen that second conduit 40 has been axially extended, which causes first conduit 30 to axially extend. The length, diameter, number of coils per inch, and resiliency of first conduit 30 is selected to prevent kinking of first conduit 30 upon extension that would block flow therethrough, yet provide for axial retraction or rebound of coil 30 upon axial contraction of outer tube 40, without compromising the performance of the unilimb circuit. Preferably, the resiliency of the coil, or tendency to recoil, should not cause disconnection of the proximal end 32 of the inner conduit 30 from proximal fitting 10 when the outer conduit 40 is axially extended to its maximum length, and likewise it should not cause the distal end 34 of inner conduit 30 to axially move with respect to the distal end of tube 40. Inner conduit 30 can be manufactured from medical grade plastic, for example, that used to provide for respiratory gas sampling, or such as that used in intravenous fluid devices.

An axially extensible and collapsible or compressible tube (e.g, accordion-like tubing, coiled tubing, etc.) used as the first tube (which may be an inner or outer tube), and wherein the second, or inner tube or adjacent tube also expands or compresses in a synchronized manner with the first tube is greatly desirable because it promotes safety, as disconnections, obstructions and kinking are diminished. This also enhances rebreathing control and provides greater flexibility and cost effectiveness as manufacturing, storage and shipping become less expensive.

Double Coil Circuit Embodiment

Figure 5A:
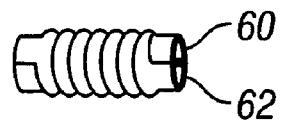
FIG. 5A-D illustrate the components and operation of systems constructed in accordance with the present invention using the double coiled circuit embodiment of the present invention.
Figure 5B:
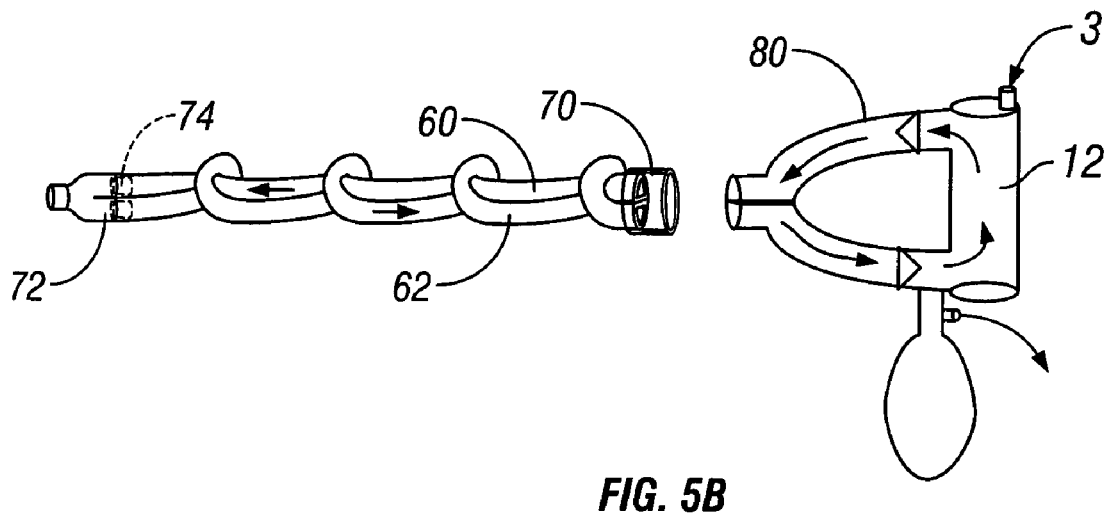

With reference to FIG. 5A-B, an embodiment of a new circuit is illustrated. Two coiled tubes 60 and 62 are in parallel-coiled relationship to form a double coil circuit. The tubes may be bonded together at one or more external points, one tube may be formed within the other, or one tube may be divided by a common wall forming two lumens. With reference to 5B, the interaction of the members upon expansion is illustrated in an exploded view, along with their alignment with a proximal fitting 70 and proximal terminal 80 used in a circle system. Flow arrows demonstrate the paths of inspiratory gases from the FGF (fresh gas flow) inlet and to the expiratory gas outlet. Tubes 60 and 62 are connected at their distal ends to a distal fitting 72 via nipples 74.

Figure 5C:
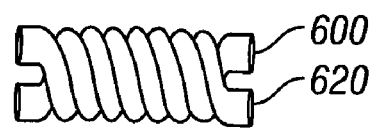
Figure 5D:
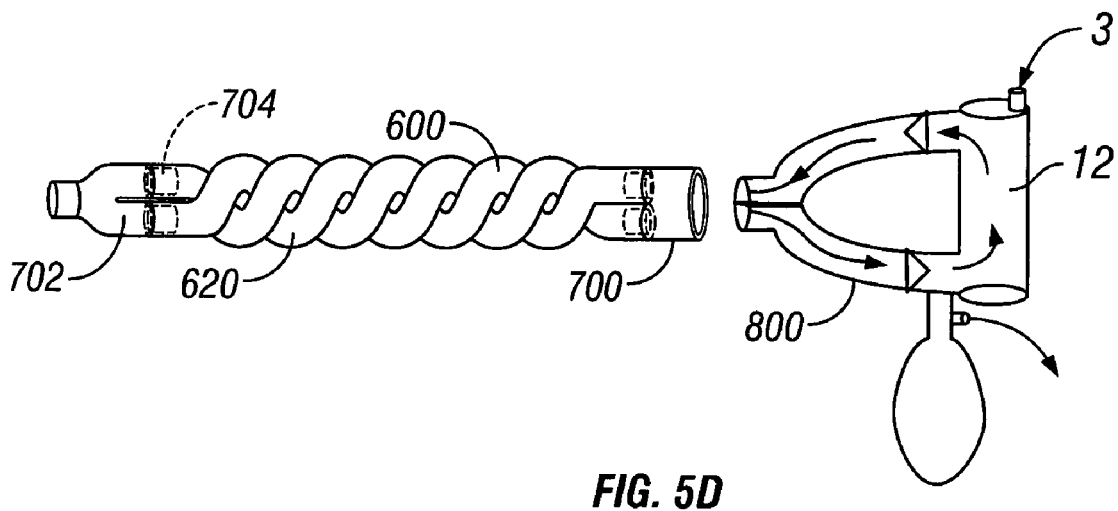

FIGS. 5C-D illustrate an alternative embodiment of the double coil illustrated in FIGS. 5A-B. Coiled tubes 600 and 620 are connected to a proximal fitting 700, which connects the respective tubes to proximal terminal 800 used in a circle system. Note that tubes 600 and 620 are interlocked by the interaction of their coils, and may optionally be periodically bonded together. As the proximal and distal openings in tubes 600 and 620 are independent, fittings can be attached on either the inside or outside of the walls of tubes 600 and 620. Tubes 600 and 620 are connected at their distal ends to a distal fitting 702 via nipples 704.

Sliding Inner Tube Circuit Embodiment

Figure 6A:
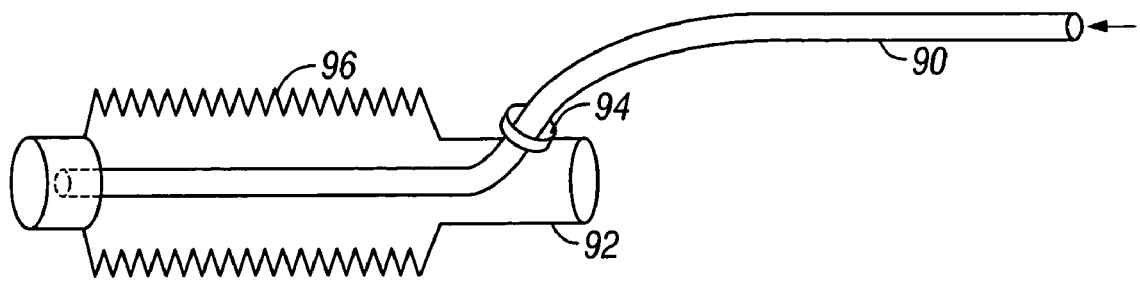
FIG. 6A-B illustrate the components and operation of the sliding inner tube embodiment of the present invention, in which a smooth-walled conventional inspiratory gas line is inserted through a fitting into an axially expandable and collapsible tube.
Figure 6B:
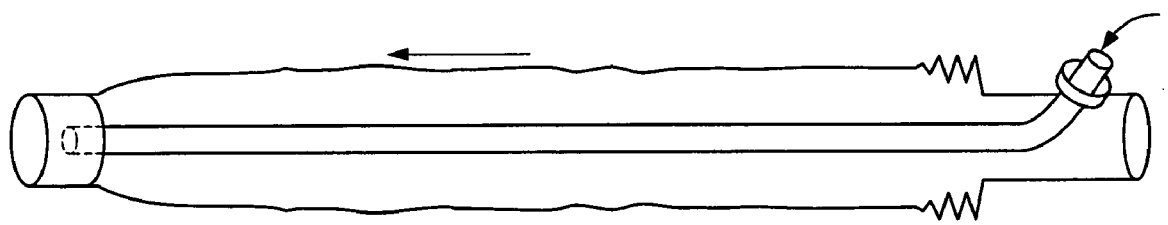

With reference to FIGS. 6 A-B, the components and operation of an embodiment of a circuit in accordance with the present invention is illustrated. A first tube 90 is slidably inserted into proximal fitting 92 via sealing fitting 94. A second tube 96 is connected at its proximal end to proximal fitting 92, with a portion of tube 96 removed to reveal the first tube 90 inside. Tube 96 is axially compressible and extendable, and may be for example made of ULTRA-FLEX® tubing. First tube 90 is provided with a smooth walled portion to permit sliding in and out of fitting 92 in response to axial contraction and extension of tube 96. The mutually axial interaction of the circuit members may be accomplished by direct connection of the distal end of tube 90 to the distal end of tube 96, via common distal fitting, or other operative connection techniques and devices.

Dual Accordion Circuit Embodiment

With reference to FIGS. 7A-D, the components and operation of an embodiment of a circuit in accordance with the present invention is illustrated in schematic form. Dual coaxial accordion (i.e., pleated) tubes 98 and 100 may be connected at their proximal ends to each other or to a proximal fitting. The tubes 98 and 100 may both be ULTRA-FLEX® tubing. Spacing flanges or perforated disks 102 may be placed between the inner and outer tubes to optimize flow. The mutually axial interaction of the circuit members may be accomplished by direct connection of the distal ends of the tubes to each other, via a common distal fitting, or other operative connection techniques and devices, for example by a spacing flange or disk 102 placed near or at the distal end of tube 98. While the embodiment in FIGS. 7A-D is coaxial, the inner tube does not need to have a common axis with the outer tube, and the distance between the axis of the inner tube and the axis of the outer tube at any given point along the length of a circuit comprising same can differ.

Flexible, axially extendable and compressible pleated tubing used for tubes 98 and 100 maintains a minimum radius, yet will also substantially maintain a length and/or angular shape to which it is manipulated. The accordion like pleats permit the tube to expand and contract to a predetermined degree associated with the amplitude of the pleats and the maximum and minimum angle formed by the annular wall portions meeting to form the pleats. The angles between the annular portions forming the pleats and the distance between the inner and outer diameter of the annular portions forming the pleats define the width of an open or closed pleat. Although in an embodiment, the annular wall portions forming the pleats are of about equal size to define a regular pleat amplitude, pleats in a tube do not necessarily all have equally sized annular wall portions forming them.

It has been surprisingly discovered that a smoother expansion/contraction, or "action," can be achieved if consideration is given to the size of the pleats used in the pleated tubing. The pleated tubing can be provided in standard lengths having integral fittings on each end to facilitate circuit construction.

Figure 7A:
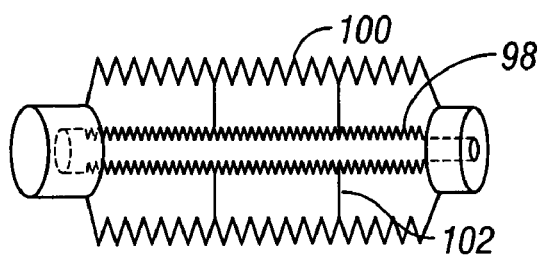
FIG. 7A-D illustrate the components and operation of a dual coaxial accordion tube embodiment of the present invention.
Figure 7B:
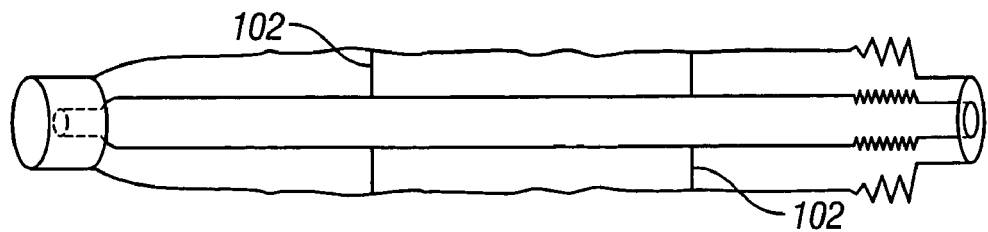
Figure 7C:
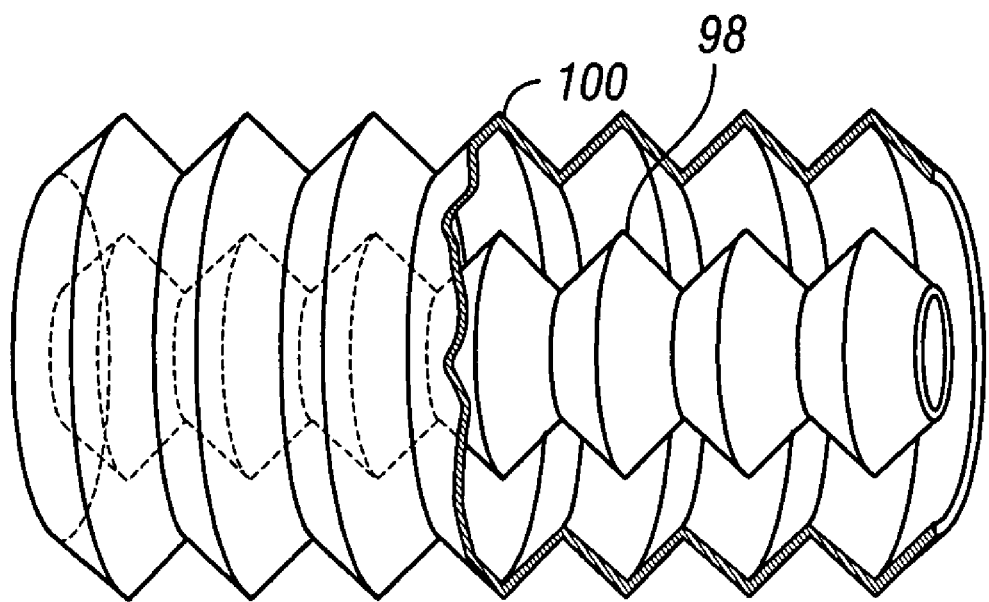
Figure 7D:
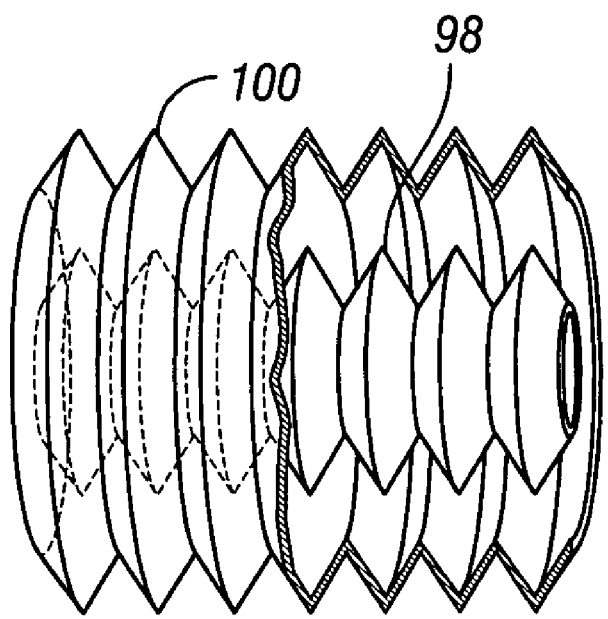

With specific reference to the embodiment illustrated in FIGS. 7C and D, the pleats in the inner tube 98 and the outer tube 100 are preferentially aligned to achieve a synchronized axial expansion and contraction of the inner and outer tubes. A lengthwise cross section of the wall of pleated tubing provides a zigzag wave pattern. The pleats each have a first compressed (or collapsed) amplitude and first wavelength shown in FIG. 7D and a second expanded amplitude and second wavelength shown in FIG. 7C. An inner pleated tube 98 that has the same expanded wavelength as the expanded wavelength of an outer pleated tube 100 may have different force requirements to contract or expand. Assuming solely for the nonlimiting purposes of example, if an inner pleated tube was more difficult to contract and open than the outer pleated tube, this could provide a different action than if the inner tube were easier to expand and contract than the outer tube. In an alternative embodiment, the open widths of the pleats can be proportional.

The tubing diameters and lengths are also selected to ensure a flow resistance low enough to meet the requirements for spontaneous and/or assisted ventilation (e.g., adequate flow, low resistance to flow). Preferably, the tubing diameters and lengths are selected to provide a resistance of less than about 6 cmH2O (pressure drop) at flow rates of up to about 60 L/min. In an embodiment, a multilumen filter forms part of the proximal fitting that can be attachable and detachable from the proximal terminal (i.e., the proximal fitting has a filter in at least two lumens. Suitable tubing can have lengths and diameters about the same as those of the inner and outer tubes in the Universal F2® circuits available from King Systems, Inc., of Nobelsville, Ind., USA.

One of skill in the art can follow the teachings of the present invention to optimize the lengths and diameters of the pleated tubing forming the inner and outer tubes for spontaneous or controlled ventilation by measuring the flow resistance at various lengths, diameters, and curvatures and/or tubing pleat wavelengths. For example, flow rates ranging from about 10 L/min to about 60 L/min can be used with various circuits having varying tubing diameters, lengths and curvatures to determine optimal pleated tubing diameters and lengths for constructing circuits and breathing systems of the present invention. A preferred dual accordion embodiment of the present invention is referred to as the Flex2TM.

Wavy Tube Circuit Embodiment

Figure 8A:
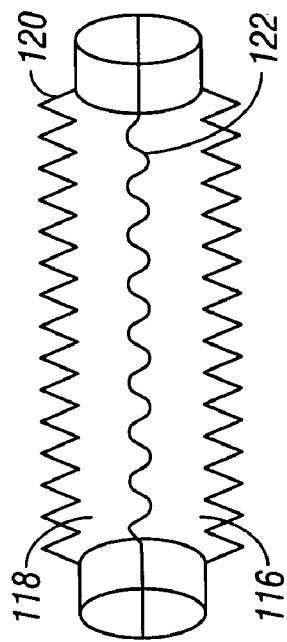
FIG. 8A-B illustrate the components and operation of a wavy tube or sheath in an accordion tube embodiment of the present invention, with a portion of the outer tube removed to reveal the inner tube.
Figure 8B:
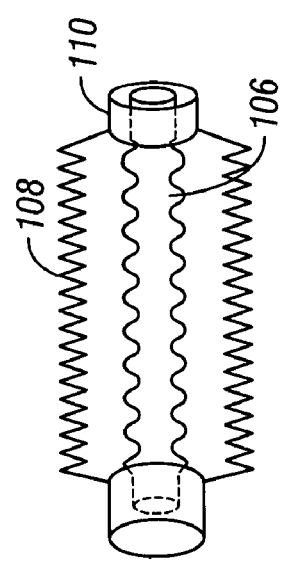

FIGS. 8A-B illustrate the components and operation of a wavy tube sheath in an accordion tube circuit embodiment of the present invention in schematic form. A relatively smooth walled tube 106 has a fixed bias to have a wavy contracted shape. Tube 106, of resilient material, can straighten when extended and return to its pre-biased contracted shape. An outer tube 108 can be extended and contracted simultaneously with tube 106. Spacing flanges or perforated disks may be placed between the inner and outer tubes to optimize flow. As with other circuit embodiments, the mutually axial interaction of the circuit members may be accomplished by direct connection of the distal end of the tubes to each other, via a common distal fitting, or other operative connection techniques and devices. Further, a variety of material can be used. For example, while tube 108 may be ULTRA-FLEX®, tube 106 may be a fabric or plastic sheath that can be elastic and radially flexible. Preferably, the axial resiliency (i.e., tendency to recoil or contract) of the inner conduits in the circuits of the present invention is insufficient to dislodge the proximal end thereof from an inspiratory gas inlet when the circuit is fully extended. For example, in drawing 8B, the tendency of tube 106 to rebound to its compressed or relaxed state, illustrated in drawing 8A, should not be sufficient to dislodge the proximal end of tube 106 from proximal fitting 110 when the fitting is held stationary and the conduits 108 and 106 extended. As noted above, tube 106 may be a fabric or plastic sheath that can be radially flexible. Thus, tube 106 may be a suave tube, and/or tube 108 may be a suave tube. For example, the inner or outer tubes of a respiratory conduit in accordance with this embodiment of the present invention may relax or collapse when not in use and expand to required patency on demand. Additional lumens can be added in this and other embodiments.

Hybrid Circuit Embodiment

Figure 9A:
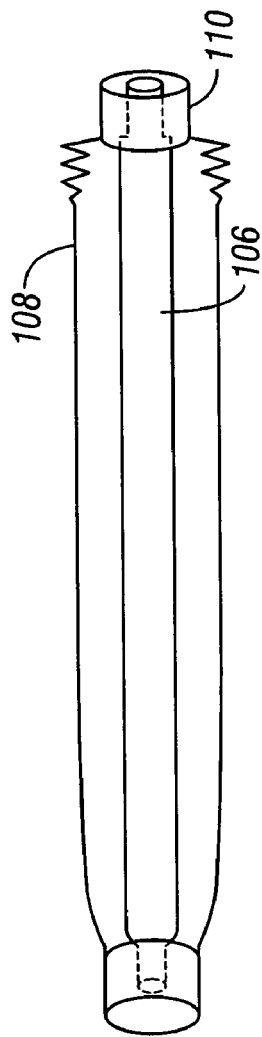
FIG. 9A-B illustrate the components and operation of a common contractile wall embodiment of the present invention, with a portion of the outer tube removed to reveal the inner tube.
Figure 9B:
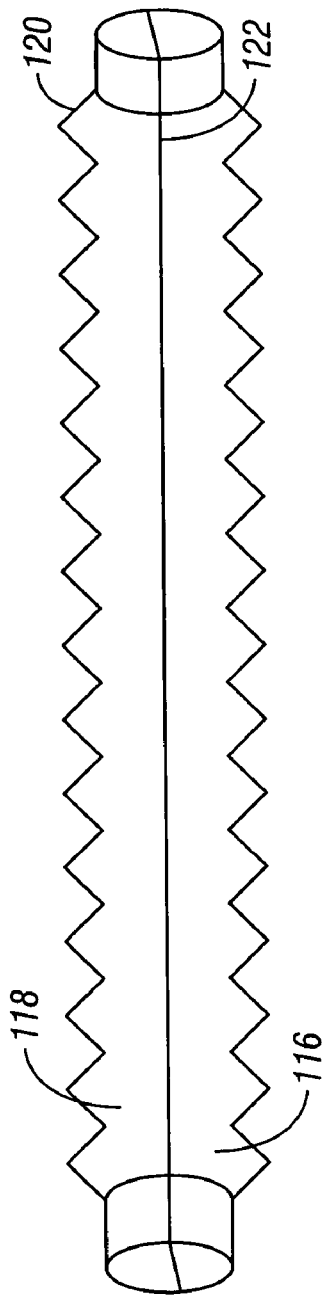

A hybrid circuit comprises conventional conduit and at least one flexible plastic sheet (e.g., polyvinyl) that forms a wall defining two or more lumens in the conduit. FIGS. 9A-B illustrate the components and operation of hybrid circuit with a common contractile wall of the present invention in schematic form. First and second tubes 116 and 118 share a common outer wall 120 that is axially expandable and contractible, and a common dividing wall 122 that can axially expand and contract with the outer wall. This embodiment may be constructed of pleated material such as that used to form ULTRA-FLEX®. Alternatively, common dividing wall 122 may be formed of a flexible plastic sheet, which permits the cross-sectional size of the two lumens to accommodate usage conditions. For. example, when pressure is higher in one lumen than the other, the wall expands into the lower-pressure lumen to make it smaller than the higher-pressure lumen, while the former lumen becomes larger. Preferably, the wall has a maximum radius under respiratory care operating conditions. Additional lumens can be included, which either share the common flexible wall, or have diameters that are independent of the diameters of the other lumens. This embodiment can be formed by cutting conventional tubing in half, and bonding a flexible plastic sheet in between the two halves, or by extruding elongated hemi-circular shaped portions of plastic, and bonding a flexible plastic sheet between matching tube halves.

Relaxed Circuit Embodiments

Figure 10:
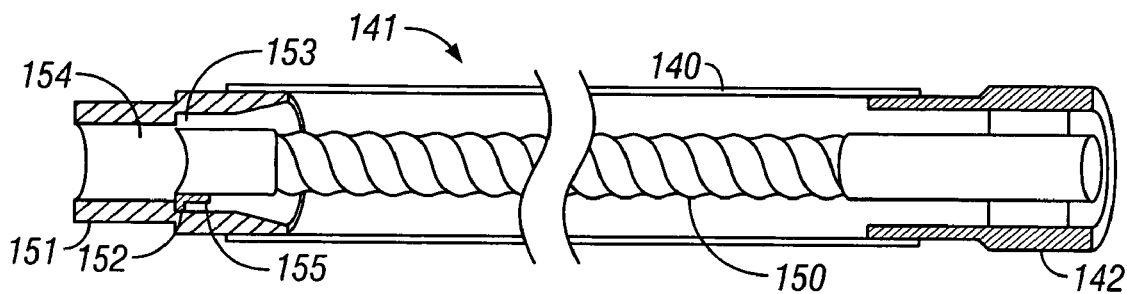
FIG. 10 illustrates the components and operation of another version of the embodiment of FIG. 8, in which a first conduit formed of a smooth plastic lamina, a suave tube, envelopes an inner tube or second conduit comprised of a corrugated tube in which the outer tube is cut away to reveal the inner tube, and an intermediate section removed to accommodate scaling of the figure. While the outer or first conduit can collapse when not being used, the inner conduit maintains its diameter during respiratory care operating conditions and during ambient and non-use conditions.

FIG. 10 illustrates the components and operation of another version of the embodiment of FIG. 8 in schematic form, in which a second conduit formed of a smooth plastic lamina, e.g., a Suave® tube, 140 envelopes an inner tube or first conduit 150 comprised of a corrugated tube. While the outer or second conduit 140 can collapse when not being used, the inner conduit 150 maintains its diameter during respiratory care operating conditions and during ambient and non-use conditions. This embodiment makes more explicit what is stated in regards to FIG. 8, in that one of the tubes can be radially flexible. In a preferred embodiment, the respiratory conduit 141 includes a proximal fitting 142 that is bonded to proximal ends of tubes 140 and 150. The proximal fitting facilitates connection to a corresponding proximal terminal. A distal fitting 151 is connected to the distal ends of tubes 140 and 150. The distal end of tube 150 is bonded to flanges 152. Radial flanges 152 are not solid annular rings, but have gaps 153 to permit flow of gases from common zone 154 into tube 140. While tube 140 may collapse under ambient, non-use conditions, in use, tube 140 may be expanded to its maximum radius and volume during expiration as well as during inspiration (depending on whether it is used for inspiration or expiration) provided there is a sufficient flow rate of gases; there is no or minimal compliance at maximum radius. Axial flanges 155 connect to radial flanges 152 and grip the distal end of inner tube 150. Tube 150 may be bonded to radial flanges. Axial extension of radial flanges. 152 and/or axial flanges 155 can provide a greater fixed dead space. As noted in other embodiments, the distal fitting, such as distal fitting 151, can be modified to provide for a sliding connection between the distal fitting main housing and the connector to the inner conduit, wherein the dead space may be adjusted to a desired volume.

Figure 11:
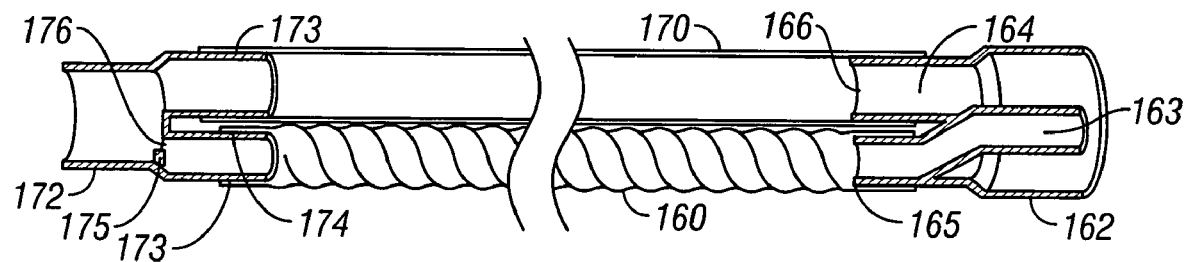
FIG. 11 illustrates the components and operation of a unilimb respiratory conduit, in which a first flexible tube is a conventional flexible corrugated or pleated tube that maintains a fixed diameter at ambient conditions and over respiratory therapy operating conditions, while the second tube is a non-conventional plastic tube that may radially collapse when patency is not required.

FIG. 11 illustrates the components and operation of a unilimb respiratory conduit in schematic form, in which a first flexible tube 160 is a conventional flexible tube that maintains a fixed diameter at ambient conditions and over respiratory therapy operating conditions, while the second tube 170 is a non-conventional plastic tube that may radially collapse when patency is not required. In a preferred embodiment, tube 170 is a suave flexible tube. A new proximal fitting 162 is illustrated, in which a coaxial flow is diverted into two independent lumens 163 and 164 that have two independent non-interfering ports 165 and 166, i.e., independent, non-interfering ports are ports that can be individually accessed without blocking or interfering with access to another port or requiring the disconnection of one port. Distal fitting 172 has axial walls 173 and 174 to which the distal ends of tubes 160 and 170 may be bonded. Extension of axial walls 173 and 174 permits for dead space adjustment. Connecting flange 175 has a gap 176 to provide for patency, while holding wall 174 in spaced relationship with wall 173.

Figure 12:
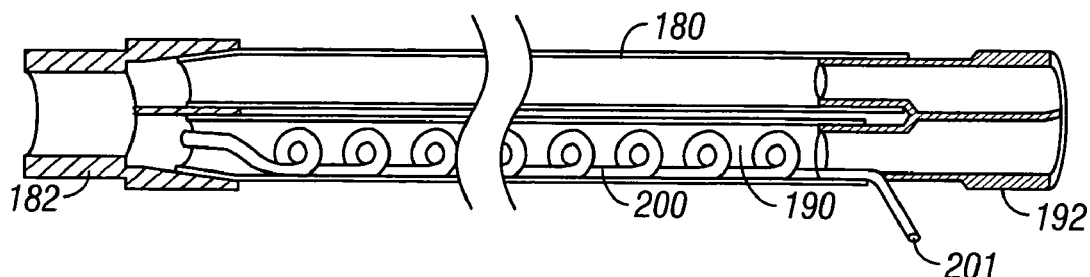
FIG. 12 illustrates the components and operation of a unilimb respiratory conduit formed of two non-conventional tubes or conduits, e.g., suave tubes, joined at their distal and proximal ends. One of the tubes includes a coiled tube, which is more radially rigid than the tube in which it is contained so as to assist in maintaining patency of its host tube.

FIG. 12 illustrates the components and operation in schematic form of a unilimb respiratory conduit formed of two non-conventional tubes or conduits 180 and 190, e.g., suave tubes, joined at their distal ends by distal fitting 182 and at their proximal ends by proximal fitting 192. Tube 190 includes a coiled tube 200, which is more radially rigid than the tube in which it is contained so as to assist in maintaining patency of its host tube. Tube 200 may be used for gas sampling or other purposes. For example, tube 190 may provide inspiratory gases. Tube 190 is held patent by the coiled tube 200, and tubes 180 and 190 are of fixed axial length. The recoiling of tube 200 causes tubes 180 and 190 to collapse axially. In an embodiment, tube 200 includes a wire of metal or plastic that maintains whatever length it is extended to rather than being axially elastic as in other embodiments. The inner wall of tube 190 is optionally bonded at periodic intervals to tube 200 so as to provide for even folding and extension of the fabric forming tube 190. In an embodiment, tube 200 is a solid wire.

Fitting 192 provides for rapid connection of the respiratory conduit to a corresponding multilumen proximal terminal. While outlet 201 of tube 200 is shown passing through the wall of fitting 192, fitting 192 may have an extra lumen for connecting tube 200 to a corresponding inlet or outlet.

The above non-limiting examples describe breathing circuits, also referred to as multilumen unilimb respiratory conduits, which axially and/or radially expand or contract. However, the breathing circuit does not need to expand or contract axially. An embodiment may comprise one fixed length conduit that is a conventional corrugated tube or a smooth resilient tube having a pipe-like configuration or an ULTRA-FLEX® tube, and the second conduit can be a non-conventional conduit. Hence, the respiratory conduit can be of fixed length, and one or more of the tubes in it may radially expand and contract.

A breathing circuit or unilimb respiratory conduit of the present invention can be readily connected to a respirator or ventilator, or to an anesthesia machine either via the proximal fitting of the respiratory conduits or via a proximal terminal, such as the one described in U.S. Pat. No. 6,003,511. By matching the proximal end of the proximal fitting to a unilimb respiratory conduit of the present invention to a corresponding proximal terminal, respiratory conduits in accordance with the present invention can be provided for quick and safe connection to a variety of respiratory devices, including but not limited to anesthesia machines and ventilator machines. This can be done directly or via a filter. A breathing circuit of the present invention can be connected to a single filter or a multilumen filter, or manufactured integrally with a monolumen or multilumen filter. The proximal end of the filter housing can be configured for quick and safe connection to a proximal terminal of a machine, and the distal end of the filter housing can match the configuration of the proximal end of the respiratory conduit.

Respiratory conduits of the present invention can also be used to ventilate patients during transport, or be connected to a gas source (e.g., oxygen source in the post-anesthesia care setting, emergency room, etc.). Thus, the breathing circuit of the present invention is a multi-purpose breathing circuit. Instead of utilizing a new device, such as an expensive ambubag for transport, the same breathing circuit of the present invention can be utilized to provide oxygenation during transportation of a patient, for example to the PACU or other location. After the patient is transported for example from the operating room to the PACU, the same breathing circuit can be utilized to oxygenate the patient in the PACU, without the need to utilize an additional oxygen supply device, such as a nasal cannula or clear oxygen mask provided with an oxygen tube or a T piece set.

Operation of Mapleson D Systems and Circle $CO_2$ Absorption Systems

With reference to FIGS. 3A-D, drawing 3A illustrates a schematic diagram of a Mapleson D system, in which the fresh gas flow ("FGF") 1 is provided via fresh gas delivery tube 2 (show in schematic form only) to a distal fitting 3. The operation of the system is better understood by reference to the numbered arrows and or part numbers. For example, during inspiration, gas to lungs 4 flows simultaneously from fresh gas flow inlet 1 and bag 7 via flow paths a and b described in the key below FIG. 3A and by reference to part numbers and numbered arrows as follows: (1→2→3→4)+(7→6→5→4). During expiration, gases flow from lungs 4 to waste gas outlet 8 via flow paths a' and b' as follows: 4→5→6→7→8.

Drawing 3B illustrates a Mapleson D type system but the fresh gas tube 2 is inserted in the proximal terminal at the proximal end of the circuit and the tube extended through breathing tube 5 to have its distal end 3 at the distal end of the circuit. In accordance with the present invention, tubes 2 and 5 can both be pleated tubing.

Drawing 3C illustrates a circle $CO_2$ absorption system, which has a $CO_2$ absorber 12, check valves (i.e., unidirectional valves) 4 and 9, as well as inspiratory conduit 5 and expiratory conduit 8 that meet at distal fitting 6. During inspiration, gas to lungs 7 flows simultaneously from fresh gas flow source 1 and bag 10 via flow paths c and d in the key below FIG. 3C as follows: (1→2→3→4→5→6→7)+(10→12→4→5→6→7). During expiration, gases flow from lungs 7 to waste gas outlet 11 via flow paths c' and d' as follows: (1→2→3→12)+(7→6→8→9→10→11).

Drawing 3D illustrates a unilimb circle $CO_2$ absorption system in which inspiratory conduit 5 is within expiratory conduit 8 distal of the proximal terminal. In accordance with the present invention, both conduits 5 and 8 can be pleated tubes and function similar to either a Universal F® or Universal F2® circuit using an F2™-type proximal terminal.

It is important to note that in the circle system, fresh gases are combined with recirculated scrubbed gases near or at the $CO_2$ absorber, and carried in a common conduit 5 to the patient. In contrast, the Mapleson D system provides the fresh gases at the distal end of the circuit.

Gas Conservation System: "F3™ Combo System"

Figure 4A:
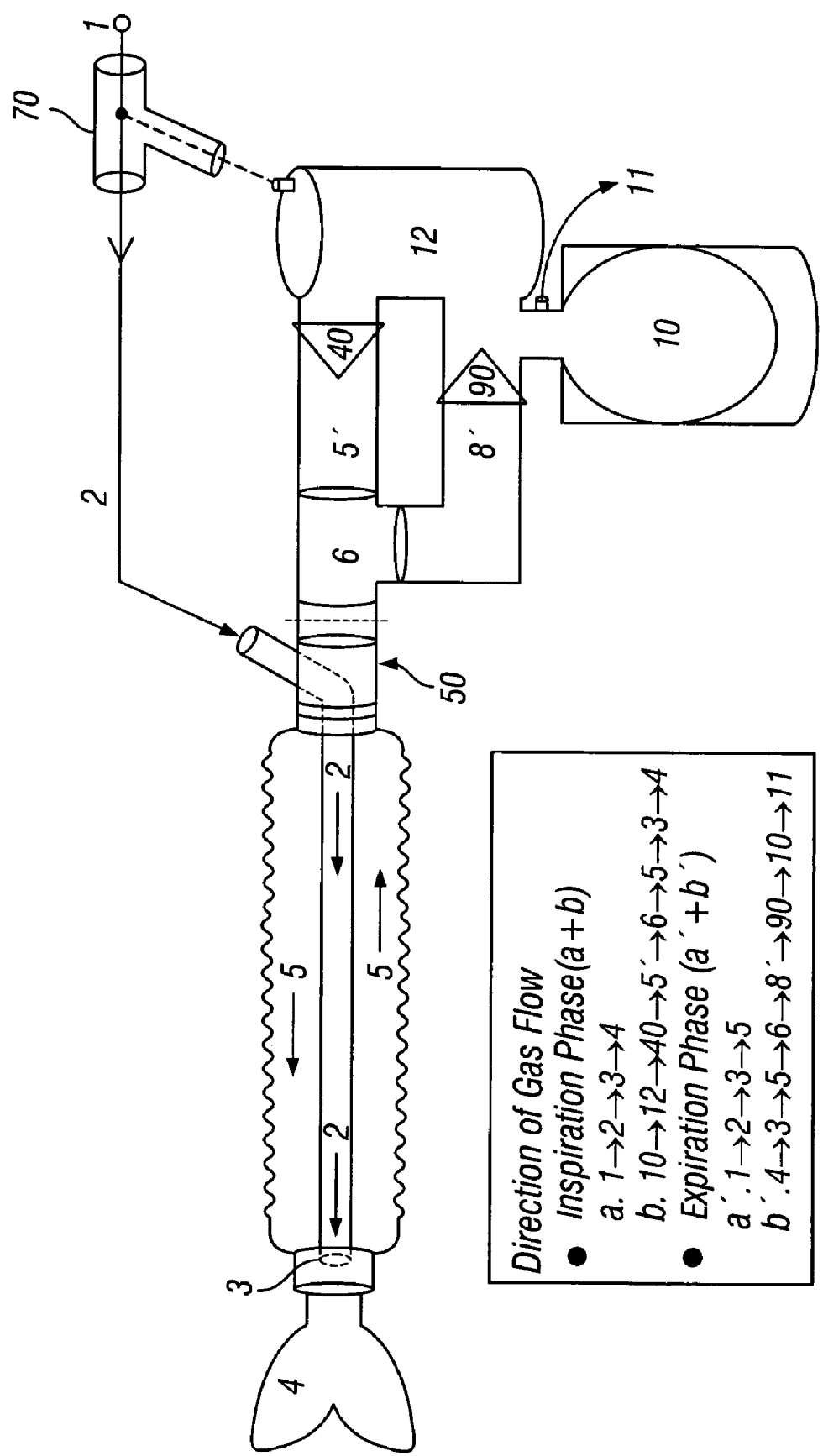

With reference to FIG. 4, drawing 4A illustrates an assisted ventilation system of the present invention utilizing an embodiment of a new breathing circuit of the present invertion. Fresh gas flow from a source 1 (e.g. an anesthesia machine) passes via flow diverter 70 through fresh gas delivery tube 2 (shown in schematic form only). Flow diverter 70 is optional as it is provided for modifying a circle system having a fresh gas input port in the scrubber circuit (generally near or at the $CO_2$ absorber). The flow diverter closes off the fresh gas input port on top of $CO_2$ absorber 12 so that fresh gases can be directly fed to the distal end 3 of the breathing conduit (i.e. FGF bypasses the scrubber module so it is not mixed with scrubbed gases). A seal could be used in place of the flow diverter, and the fresh gas source could come from a variety of locations. In this embodiment, tube 2 is, as with a Bain, rigidly bonded to proximal fitting 50, and fresh gases are delivered directly to the distal end 3 of the breathing circuit, which continuously feed the common inspiratory/expiratory conduit 5, also referred to as a rebreathing tube. However, with reference to drawing 4C, unlike a Bain, the dimensions of conduit 5 can be altered so that the tube volume and the concentration of its contents are altered so that the inspired concentration of gases can be adjusted for each patient, and rebreathing can be controlled. For example, tube 5 may be an ULTRA-FLEX® tube (i.e., a pleated tube). Control can be achieved by adjusting the dimensions of tube 5, for example by axially adjusting the length of tube 5 (titration of tube volumes and contents in response to inspired and/or end-tidal gas concentration data provided by the monitoring equipment).

Note that unlike the conventional circle system, in the new system of the present invention the fresh gases delivered directly from the anesthesia machine are not mixed or diluted at the machine/scrubber circuit end (i.e., proximally of the inspiratory valve). Because the fresh gas flow is delivered close to the patient, the inspired anesthetic concentrations ($F_I$) are almost equal to the delivered concentrations ($F_D$). Thus, the anesthetist can rely on the anesthetic concentrations reported by the flow meter and the vaporizer as indicative of the inspired concentrations. In contrast to the Mapleson D system, in the new system the expired gases are not all disposed of but are reused as "refreshed gas," as expired gases pass through a scrubber module for recirculation. This new "F system" provides a surprising improvement in the control and quality of respiratory and anesthetic ventilation while avoiding waste of anesthetic gases.

If a coiled fresh gas tube is used, upon contraction of tube 5, tube 2 coils to contract, as can be seen in FIG. 4 C. The fresh gas tube 2 can have other shapes and can be arranged to be an inner or outer tube with respect to tube 5. If tube 2 is smooth-walled, it can slide in and out of a fitting as shown in FIG. 6.

Alternatively, with further reference to FIGS. 7A-D, fresh gases can be provided in the circuit via an inner tube 98 that is a pleated tube. Preferably, the volume of tube 5 during use is adjusted to be larger than the tidal volume ($V_T$) to minimize mixing of the fresh gases with the "scrubbed gases". This allows optimal utilization of the fresh gases (anesthetic agents) as well as O2 and CO2 rebreathing control.

In a preferred embodiment, the length of the rebreathing tube may be variable for multiple usages. The same breathing system may be universally used, in an operating room, ICU, emergency room, respiratory care ward, in adult and pediatric cases, etc.

Drawing 4B illustrates a proximal terminal 52 in schematic form that may be separately detached and connected to breathing conduit 5 and fresh gas tube 2. An additional proximal terminal 6 is also shown in schematic form. Terminal 6 can be an F2® type or Y adaptor. Referring back to drawing 4A, the system components also preferably includes a reservoir bag or ventilator device 10, waste gas outlet 11, which may be attached to a scavenger, $CO_2$ absorber 12, check valves 40 and 90, inspiratory conduit 5', expiratory conduit 8', and a proximal terminal 6 that connects to proximal fitting 50.

The operation of the system is better understood by reference to the numbered arrows and or part numbers. For example, in a preferred embodiment, during inspiration, gas to lungs 4 flows simultaneously from fresh gas flow source 1 and bag/ventilator 10 as follows: (1→2→3→4)+(10→12→40→5'→6→5→3→4). During expiration, gases flow from lungs 4 to waste gas outlet 11 as follows: (1→2→3→5)+(4→3→5→6→8'→90→10→11).

Thus, in a preferred embodiment, a new ventilation and anesthesia system is provided, comprising a recirculation module, a rebreathing tube operatively connected at its proximal end opening to the recirculation module for providing expired gases to and receiving gases from the recirculation module, and a distal input for fresh gases, wherein the distal input is located in the distal portion of the rebreathing tube or in a distal fitting operatively connected to the distal end of the rebreathing tube. The recirculation module preferably includes a scrubbing circuit, which may include at least two unidirectional valves, an expiratory input conduit, CO2 absorber, exhaust vent, scrubbed gas output conduit, and squeeze bag and/or ventilator. In a preferred embodiment, a filter device can be detachably connected at the proximal end of the rebreathing conduit 5; the filter device may also be integrally formed with conduit 5. A preferred embodiment of this new system is referred to as an F3™ COMBO system.

A System that Optimizes Utilization of Fresh Gases that is also more Efficient and Safer It is well recognized that methods of low flow anesthesia have considerable advantages over high flow anesthesia methods because they reduce the amount of wasted anesthetic gases, therefore, they are more economic and reduce healthcare costs. Moreover, such methods maintain better humidification and temperature of the inhaled gases. They also minimize the amount of gas released from the system to the environment, reducing operating room pollution, which provides a safer working environment and in general less air pollution. However, despite numerous advantages of low flow anesthesia techniques, the use of these methods and associated systems is hampered by numerous limitations that make them unsafe. Therefore, there is a need to improve these systems and methods.

Traditionally, high fresh gas flow, defined as flow greater than five liters per minute (FGF>5 L/min), has been used in a conventional anesthesia circle breathing system with $CO_2$ absorption, and over 7 L/min in the Mapleson D system. However, more than 90% of the newly delivered fresh gases are wasted. One of the main reasons for high flow anesthesia practice is the fear of over-dosing or under-anesthetizing the patient when low flow anesthesia is provided. With high fresh gas flows, the inspired (anesthetic) gas concentration (FI or $F_1$) can be assumed to be equivalent to the delivered gas concentration (FD or $F_D$=vaporizer setting concentration). Such an assumption cannot be made with low flow anesthesia. Lowering the FGF results in a gradually increasing gradient (difference) between the delivered gas concentration (FD) and the patient's inspired gas (FI), which is in part due to the increasing dilution of the fresh gas with the scrubbed gases within the system. For example, during low FGF of less than 3 L/min, there are significant discrepancies (over 20%) between the inspired gas concentration and the delivered gas concentration. This may result in under-anesthetized patients. Therefore, low flow anesthesia has not been recommended unless continuous flow adjustments are made during anesthesia and by very careful monitoring the inspiratory and the end-tidal gas concentrations.

The examples section from the parent application, which is incorporated by reference but not repeated here in order to shorten the application and expedite prosecution, supports the hypothesis that low flow anesthesia can be safely administered by using the F3 COMBO™ system, and over-dosing or under-dosing of anesthetics can be avoided.

With the present F3 COMBO™ system, the anesthetist will be able to better control the inspired concentration of anesthetic gases in a more accurate and predictable manner. Therefore, even in the absence of expensive multi-gas monitoring equipment, a safe and reliable low flow anesthesia can be achieved. Also, recovery from anesthesia can be accelerated at the end of surgery and anesthesia. This can be accomplished by providing high flows of oxygen directly at the distal end so that the residual anesthetic in the lungs and the breathing circuit will be washed out very quickly. Quick recovery from anesthesia can save anesthesia recovery time and money. Therefore, the F3 COMBO™ circuit and/or methods for utilizing same can conserve anesthetic gases as well as oxygen, while minimizing pollution and health hazards, and thus improve breathing/anesthesia system efficiency. This will result in an overall lower health care costs, while optimizing patient health care.

As is now clear, the present invention provides a method of providing assisted ventilation or anesthesia wherein fresh gases are provided at low flow, for example a volume of about 1 liter per minute (flows considered low range from about 0.5 to less than 5 L/min, or less than 3 L/min in preferred embodiments), and the $F_I/F_D$ concentration ratio can be maintained at a desired level, for example above about 0.80 or higher, by adjusting the volume of the rebreathing tube proximal of the fresh gas input. In a preferred embodiment, fresh gas flows from about 1 to about 3 L/min are used, and more preferably from about 1 to about 2 L/min.

Figure 13A:
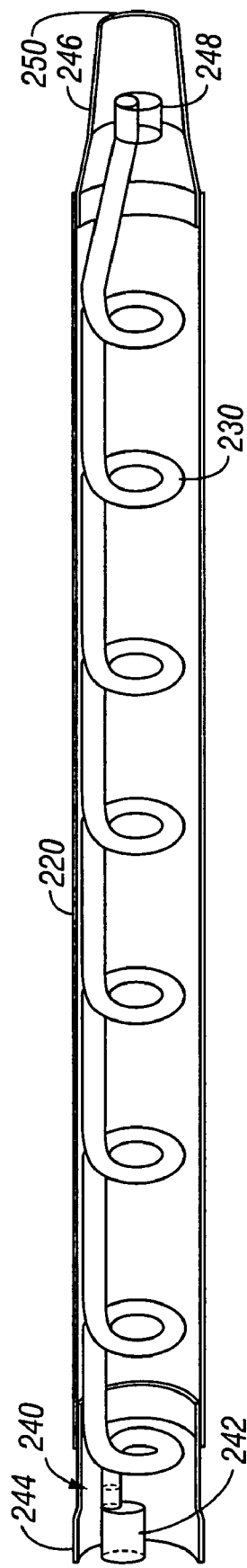
FIGS. 13(a) and (b) illustrate a respiratory conduit in expanded form (a) and compressed form (b), in which the outer or first conduit is a suave tube with a portion removed to reveal the inner tube, and the inner conduit is a coiled tube wherein the coiled tube lumen has a relatively rigid cross-sectional shape.
Figure 13B:
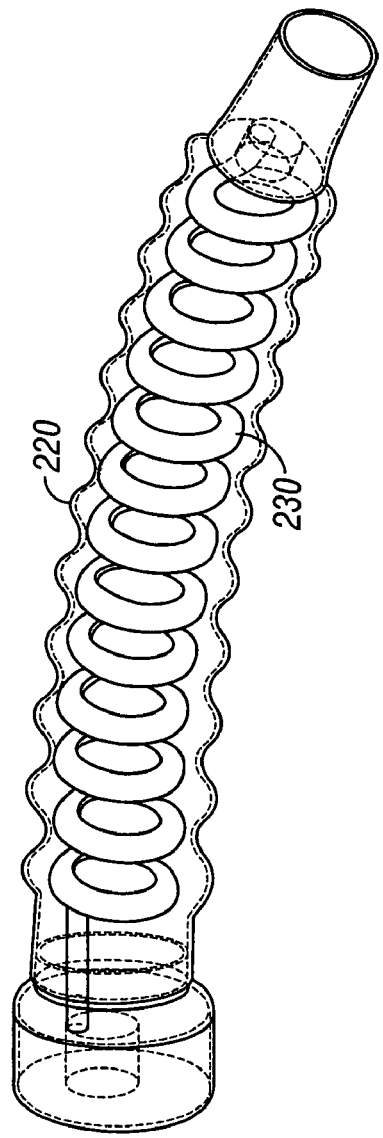

As can be seen by the unilimb respiratory conduit illustrated in FIGS. 13 (*a*) and (*b*), multilumen conduits of the present invention come in a variety of forms, and can be compressed into relatively small volumes for shipping and storage.

With further reference to FIG. 13, a respiratory conduit is shown in expanded form (a) and in compressed form (b). An outer or first conduit 220 is a suave tube, and the inner conduit 230 is a coiled tube wherein the coiled tube lumen has a relatively rigid cross-sectional shape. When compressed, excess fabric in suave tube 220 takes on a ruffled or wrinkled appearance. The wrinkles may be evenly distributed by periodic attachment of tube 220 to inner tube 230. Proximal fitting 240 is coaxial, with the distal end of coiled tube 230 being bonded to an inner pipe 242 or being integral therewith, although other variations are possible.

In an alternative embodiment, a rigid inner pipe and rigid outer pipe are held together by rigid spacing means to form a proximal fitting to which inner and outer conduits can be connected. Thus, the present invention allows for optimization of respiratory conduit manufacture that can depend upon the machinery, parts, materials, and skills available. Inner pipe 242 can be integrally formed with rigid coil 230 in one step. In another step, inner pipe 242, integrally formed to coil 230, can be bonded to an outer pipe, such as pipe 244, with appropriate spacing means. A suave tube can then be bonded to outer pipe 244. A single distal fitting 246, with an inner member 248 and an outer member 250 can be bonded to the corresponding tubes prior to bonding of the suave tube to the proximal fitting. The distal fitting 246 can also be constructed in a series of steps as it is connected to the tubes. For example, inner member 246 can be integrally formed to the distal end of tube 230 when the proximal end of tube 230 is bonded to inner pipe 242. Various combinations of construction steps are possible.

It should be clear to one of skill in the art that the F3™ circuits described herein are not limited to a unilimb tubing arrangements, but can also use dual limb arrangements in which at least one tube is a suave or coiled tube, which can lead to significant reduced costs in manufacturing, shipping and storage.

Thus, exemplary embodiments and uses of the present inventions have been described. Alternative embodiments, descriptions and terms are contemplated. For example, the conduits in the circuit may be of different sizes from one another, and more than two lumens may be present. Using the present invention, larger or smaller diameter conduits may be used, and both circle circuit and Mapleson type circuits may be constructed.

While exemplary embodiments of the present invention have been set forth above, it is to be understood that the pioneer inventions disclosed herein may be constructed or used otherwise than as specifically described.

The invention claimed is:

1. A unilimb multilumen respiratory circuit comprising first and second conduits, each of said conduits having a proximal and a distal end, wherein said proximal end of said first conduit can be operatively connected to an inlet for respiratory gases and said second conduit can be operatively connected to an outlet for respiratory gases, wherein said first conduit comprises pleated tubing and said second conduit comprises pleated tubing, said conduits being connected at their distal ends to a common distal fitting, wherein said first and second conduits meet the flow requirements and compliance required for spontaneous and assisted ventilation, and wherein said distal fitting can be detachably connected directly to a patient airway device selected from the group consisting of a mask, an endotracheal tube, a laryngeal mask, a laryngeal tube, and a nasal tube, wherein axial extension or contraction of said distal end of said second conduit causes a corresponding axial extension or contraction of said distal end of said first conduit, wherein upon axial extension of said distal end of said second conduit from a first compressed axial conformation to a second expanded axial conformation, or vice versa, said second conduit will retain said second conformation, and wherein said first conduit will expand or contract in length with corresponding axial expansion or contraction of said second conduit, wherein said proximal end of said first conduit is connected to said proximal end of said second conduit via a common proximal fitting or proximal terminal, wherein axial extension or contraction will adjust the volume therein of at least one of said first second conduits.

2. The circuit of claim 1, wherein the length of said first tube can be longer than said second tube when the length of said first tube is not constrained by mutual connection with said second tube to said fittings or said distal filling and said proximal terminal.

3. The circuit of claim 1, wherein the amplitudes or wavelengths of the pleats of said first and second tube are proportional in size.

4. The circuit of claim 1, wherein said first and second conduits have resistance to flow of less than about 6 cm H2O at flow rates of up to about 60 L/min.

5. The circuit of claim 1, wherein at least a portion of said first conduit is contained within said second conduit.

6. The circuit of claim 5, wherein said at least a portion of said first conduit contained within said second conduit is coaxial therewith.

7. A ventilation or anesthesia system, comprising the unilimb multilumen respiratory circuit of claim 6.

8. The circuit of claim 5, wherein said proximal fitting or proximal terminal comprises at least two lumens each having filters therein to provide for independent filtration of fluid passing to or from said first and second conduits via said proximal fitting or proximal terminal.

9. The circuit of claim 1, wherein said proximal fitting or proximal terminal comprises at least two lumens each having filters therein to provide for independent filtration of fluid passing to or from said first and second conduits via said proximal fitting or proximal terminal.

10. A ventilation or anesthesia system, comprising the unilimb multilumen respiratory circuit of claim 9.

11. A ventilation or anesthesia system, comprising the unilimb multilumen respiratory circuit of claim 1.

* * * * *

UNITED STATES PATENT AND TRADEMARK OFFICE
CERTIFICATE OF CORRECTION

PATENT NO. : 7,261,105 B2 Page 1 of 1
APPLICATION NO. : 10/777772
DATED : August 28, 2007
INVENTOR(S) : Atsuo F. Fukunaga, Blanca M. Fukunaga and Alex S. Fukunaga It is certified that error appears in the above-identified patent and that said Letters Patent is hereby corrected as shown below:

Col. 22 Claim 1, line 29, change "said first second conduits" to --said first or second conduits--.

Signed and Sealed this

Thirteenth Day of November, 2007

JON W. DUDAS
*Director of the United States Patent and Trademark Office*